United States Patent
Rufner et al.

(10) Patent No.: US 9,265,545 B2
(45) Date of Patent: Feb. 23, 2016

(54) ANTIOXIDANT STABILIZED CROSSLINKED ULTRA-HIGH MOLECULAR WEIGHT POLYETHYLENE FOR MEDICAL DEVICE APPLICATIONS

(71) Applicant: Zimmer, Inc., Warsaw, IN (US)

(72) Inventors: Alicia Rufner, Columbia City, IN (US); John Knight, Warsaw, IN (US); Toni Rowe, Bremen, IN (US); Dirk Pletcher, Walkerton, IN (US); Ray Gsell, Winona Lake, IN (US); Hallie E Brinkerhuff, Winona Lake, IN (US); Werner Schneider, Rafz (CH)

(73) Assignee: Zimmer, Inc., Warsaw, IN (US)

( * ) Notice: Subject to any disclaimer, the term of this patent is extended or adjusted under 35 U.S.C. 154(b) by 85 days.

(21) Appl. No.: 14/157,708

(22) Filed: Jan. 17, 2014

(65) Prior Publication Data

US 2014/0194935 A1 Jul. 10, 2014

Related U.S. Application Data

(63) Continuation of application No. 13/403,040, filed on Feb. 23, 2012, now Pat. No. 8,669,299, which is a continuation of application No. 12/579,094, filed on Oct. 14, 2009, now Pat. No. 8,129,440, which is a continuation of application No. 12/100,894, filed on Apr. 10, 2008, now abandoned.

(60) Provisional application No. 60/922,738, filed on Apr. 10, 2007.

(51) Int. Cl.
| | |
|---|---|
| *A61L 27/16* | (2006.01) |
| *A61B 17/80* | (2006.01) |
| *A61L 27/50* | (2006.01) |
| *C08L 23/06* | (2006.01) |

(52) U.S. Cl.
CPC ............ *A61B 17/8085* (2013.01); *A61L 27/16* (2013.01); *A61L 27/505* (2013.01); *C08L 23/06* (2013.01); *C08L 2312/06* (2013.01); *Y10T 428/31* (2015.01); *Y10T 428/315* (2015.01)

(58) Field of Classification Search
None
See application file for complete search history.

(56) References Cited

U.S. PATENT DOCUMENTS

| | | | |
|---|---|---|---|
| 5,414,049 A | 5/1995 | Sun et al. | |
| 5,577,368 A | 11/1996 | Hamilton et al. | |
| 5,721,334 A | 2/1998 | Burstein et al. | |
| 5,753,182 A | 5/1998 | Higgins | |
| 5,824,411 A | 10/1998 | Shalaby et al. | |
| 5,827,904 A | 10/1998 | Hahn | |
| 5,879,400 A | 3/1999 | Merrill et al. | |
| 6,017,975 A | 1/2000 | Saum et al. | |
| 6,087,553 A | 7/2000 | Cohen et al. | |
| 6,087,559 A | 7/2000 | Nichols | |
| 6,156,845 A | 12/2000 | Saito et al. | |
| 6,184,265 B1 | 2/2001 | Hamilton et al. | |
| 6,228,900 B1 | 5/2001 | Shen et al. | |
| 6,231,804 B1 | 5/2001 | Yamauchi et al. | |
| 6,242,507 B1 | 6/2001 | Saum et al. | |
| 6,245,276 B1 | 6/2001 | McNulty et al. | |
| 6,277,390 B1 | 8/2001 | Schaffner | |
| 6,432,349 B1 | 8/2002 | Pletcher et al. | |
| 6,437,048 B1 | 8/2002 | Saito et al. | |
| 6,448,315 B1 | 9/2002 | Lidgren et al. | |
| 6,464,926 B1 | 10/2002 | Merrill et al. | |
| 6,503,439 B1 | 1/2003 | Burstein | |
| 6,558,794 B1 | 5/2003 | Fehrenbacher et al. | |
| 6,562,540 B2 | 5/2003 | Saum et al. | |
| 6,620,198 B2 | 9/2003 | Burstein et al. | |
| 6,627,141 B2 | 9/2003 | McNulty et al. | |
| 6,641,617 B1 | 11/2003 | Merrill et al. | |
| 6,664,308 B2 | 12/2003 | Sun et al. | |
| 6,664,317 B2 | 12/2003 | King, III | |
| 6,692,679 B1 | 2/2004 | McNulty et al. | |
| 6,786,933 B2 | 9/2004 | Merrill et al. | |
| 6,818,020 B2 | 11/2004 | Sun et al. | |
| 6,818,172 B2 | 11/2004 | King et al. | |
| 6,852,772 B2 | 2/2005 | Muratoglu et al. | |
| 6,853,772 B2 | 2/2005 | Battiato et al. | |
| 6,872,764 B2 | 3/2005 | King, III | |

(Continued)

FOREIGN PATENT DOCUMENTS

| | | |
|---|---|---|
| AU | 2006283596 A1 | 1/2007 |
| AU | 2006350369 A1 | 8/2008 |

(Continued)

OTHER PUBLICATIONS

Badertscher, Polymer Degradation and Stability, 97 (2012) 2255-2261.*

(Continued)

*Primary Examiner* — Robert C Boyle
(74) *Attorney, Agent, or Firm* — Schwegman Lundberg & Woessner, P.A.

(57) ABSTRACT

An antioxidant combined with UHMWPE prior to subjecting the UHMWPE to crosslinking irradiation. In one exemplary embodiment, the antioxidant is tocopherol. After the antioxidant is combined with the UHMWPE, the resulting blend may be formed into slabs, bar stock, and/or incorporated into a substrate, such as a metal, for example. The resulting product may then be subjected to crosslinking irradiation. In one exemplary embodiment, the UHMWPE blend is preheated prior to subjecting the same to crosslinking irradiation. Once irradiated, the UHMWPE blended product may be machined, packaged, and sterilized in accordance with conventional techniques.

16 Claims, 3 Drawing Sheets

(56) References Cited

U.S. PATENT DOCUMENTS

| | | |
|---|---|---|
| 6,933,026 B2 | 8/2005 | Mauze et al. |
| 7,094,472 B2 | 8/2006 | Du Plessis et al. |
| 7,160,492 B2 | 1/2007 | King |
| 7,166,650 B2 | 1/2007 | Muratoglu et al. |
| 7,214,764 B2 | 5/2007 | King |
| 7,259,198 B2 | 8/2007 | Vaillant |
| 7,304,097 B2 | 12/2007 | Muratoglu et al. |
| 7,335,697 B2 | 2/2008 | King et al. |
| 7,384,430 B2 | 6/2008 | Greer et al. |
| 7,431,874 B2 | 10/2008 | Muratoglu et al. |
| 7,435,372 B2 | 10/2008 | Mimnaugh et al. |
| 7,445,641 B1 | 11/2008 | Ornberg et al. |
| 7,498,365 B2 | 3/2009 | Muratoglu et al. |
| 7,507,774 B2 | 3/2009 | Muratoglu et al. |
| 7,569,620 B2 | 8/2009 | Muratoglu et al. |
| 7,615,075 B2 | 11/2009 | Kunze et al. |
| 7,635,725 B2 | 12/2009 | Ballare et al. |
| 7,683,133 B2 | 3/2010 | King et al. |
| 7,790,095 B2 | 9/2010 | Muratoglu et al. |
| 7,806,064 B2 | 10/2010 | Wellman |
| 7,833,452 B2 | 11/2010 | Muratoglu et al. |
| 7,846,376 B2 | 12/2010 | Abt et al. |
| 7,863,348 B2 | 1/2011 | Abt et al. |
| 8,129,440 B2 | 3/2012 | Rufner et al. |
| 8,178,594 B2 | 5/2012 | Rufner et al. |
| 8,470,903 B2 | 6/2013 | Abt et al. |
| 8,664,290 B2 | 3/2014 | Rufner et al. |
| 8,669,299 B2 | 3/2014 | Rufner et al. |
| 8,673,202 B2 | 3/2014 | Abt et al. |
| 2001/0027345 A1 | 10/2001 | Merrill et al. |
| 2001/0049401 A1 | 12/2001 | Salovey et al. |
| 2002/0007219 A1 | 1/2002 | Merrill et al. |
| 2002/0156536 A1 | 10/2002 | Harris et al. |
| 2003/0013781 A1 | 1/2003 | Merrill et al. |
| 2003/0045603 A1 | 3/2003 | Salovey et al. |
| 2003/0105182 A1 | 6/2003 | Merrill et al. |
| 2003/0119935 A1 | 6/2003 | Merrill et al. |
| 2003/0127778 A1 | 7/2003 | Scott et al. |
| 2003/0149125 A1 | 8/2003 | Muratoglu et al. |
| 2003/0158287 A1 | 8/2003 | Salovey et al. |
| 2003/0212161 A1 | 11/2003 | McKellop et al. |
| 2004/0051213 A1 | 3/2004 | Muratoglu et al. |
| 2004/0156879 A1* | 8/2004 | Muratoglu et al. ........... 424/423 |
| 2004/0265165 A1 | 12/2004 | King |
| 2005/0006821 A1 | 1/2005 | Merrill et al. |
| 2005/0056971 A1 | 3/2005 | Merrill et al. |
| 2005/0059750 A1 | 3/2005 | Sun et al. |
| 2005/0096749 A1 | 5/2005 | Merrill et al. |
| 2005/0124718 A1 | 6/2005 | Muratoglu et al. |
| 2005/0125074 A1 | 6/2005 | Salovey et al. |
| 2005/0146070 A1 | 7/2005 | Muratoglu et al. |
| 2005/0165495 A1 | 7/2005 | Merrill et al. |
| 2005/0194722 A1 | 9/2005 | Muratoglu et al. |
| 2005/0194723 A1 | 9/2005 | Muratoglu et al. |
| 2005/0267594 A1 | 12/2005 | Merrill et al. |
| 2006/0079597 A1 | 4/2006 | Muratoglu et al. |
| 2006/0115668 A1 | 6/2006 | King et al. |
| 2006/0264541 A1 | 11/2006 | Lederer et al. |
| 2007/0004818 A1 | 1/2007 | Muratoglu et al. |
| 2007/0043137 A1 | 2/2007 | Muratoglu et al. |
| 2007/0059334 A1 | 3/2007 | Abt et al. |
| 2007/0077268 A1 | 4/2007 | King et al. |
| 2007/0114702 A1 | 5/2007 | Muratoglu et al. |
| 2007/0149660 A1 | 6/2007 | Kumar et al. |
| 2007/0191504 A1 | 8/2007 | Muratoglu |
| 2007/0232762 A1 | 10/2007 | Ernsberger et al. |
| 2007/0265369 A1 | 11/2007 | Muratoglu et al. |
| 2007/0267030 A1 | 11/2007 | Muratoglu et al. |
| 2007/0275030 A1 | 11/2007 | Muratoglu et al. |
| 2007/0293647 A1 | 12/2007 | McKellop et al. |
| 2008/0039545 A1 | 2/2008 | Muratoglu et al. |
| 2008/0067724 A1 | 3/2008 | Muratoglu et al. |
| 2008/0090933 A1 | 4/2008 | Muratoglu et al. |
| 2008/0090934 A1 | 4/2008 | Muratoglu et al. |
| 2008/0119582 A1 | 5/2008 | Muratoglu et al. |
| 2008/0133018 A1 | 6/2008 | Salovey et al. |
| 2008/0133021 A1 | 6/2008 | Shen et al. |
| 2008/0139137 A1 | 6/2008 | Guo et al. |
| 2008/0140196 A1 | 6/2008 | Schroeder et al. |
| 2008/0214692 A1 | 9/2008 | Muratoglu et al. |
| 2008/0215142 A1 | 9/2008 | Muratoglu et al. |
| 2008/0262120 A1 | 10/2008 | Muratoglu |
| 2008/0274161 A1 | 11/2008 | Muratoglu et al. |
| 2008/0293856 A1 | 11/2008 | Kumar et al. |
| 2008/0318022 A1 | 12/2008 | James et al. |
| 2008/0319137 A1* | 12/2008 | Rufner et al. ............. 525/333.7 |
| 2009/0030524 A1 | 1/2009 | Schroeder et al. |
| 2009/0105364 A1 | 4/2009 | Merrill et al. |
| 2009/0118390 A1 | 5/2009 | Abt et al. |
| 2009/0192610 A1 | 7/2009 | Case et al. |
| 2009/0265001 A1 | 10/2009 | Muratoglu et al. |
| 2009/0281624 A1 | 11/2009 | Conteduca et al. |
| 2010/0029858 A1 | 2/2010 | Rufner et al. |
| 2010/0082101 A1 | 4/2010 | Muratoglu et al. |
| 2010/0137481 A1 | 6/2010 | Shen et al. |
| 2010/0190882 A1 | 7/2010 | Muratoglu et al. |
| 2011/0028600 A1 | 2/2011 | Rufner et al. |
| 2011/0306698 A1 | 12/2011 | Pletcher |
| 2012/0070600 A1 | 3/2012 | Muratoglu et al. |
| 2012/0157591 A1 | 6/2012 | Rufner et al. |
| 2014/0135415 A1 | 5/2014 | Abt et al. |
| 2014/0194934 A1 | 7/2014 | Rufner et al. |

FOREIGN PATENT DOCUMENTS

| | | |
|---|---|---|
| AU | 2008236996 A1 | 10/2008 |
| AU | 2012203503 B2 | 5/2014 |
| CA | 2619937 A1 | 3/2007 |
| CA | 2669386 A1 | 8/2008 |
| CA | 2619502 C | 11/2012 |
| CS | 221403 B1 | 4/1983 |
| CZ | 221405 B1 | 2/1986 |
| EP | 0560279 A1 | 9/1993 |
| EP | 0727195 A2 | 8/1996 |
| EP | 0995449 A1 | 4/2000 |
| EP | 0560279 B1 | 6/2000 |
| EP | 0727195 B1 | 8/2002 |
| EP | 1421918 A1 | 5/2004 |
| EP | 1647242 A1 | 4/2006 |
| EP | 0935446 B1 | 2/2007 |
| EP | 1421918 B1 | 4/2008 |
| EP | 1647242 B1 | 5/2008 |
| EP | 1924614 A2 | 5/2008 |
| EP | 2046577 A1 | 4/2009 |
| EP | 2083981 A1 | 5/2009 |
| EP | 2150285 A2 | 2/2010 |
| EP | 2150285 B1 | 2/2012 |
| EP | 2277560 B1 | 10/2013 |
| EP | 2172229 B1 | 7/2014 |
| JP | 11239611 A | 9/1999 |
| JP | 2006515777 A | 6/2006 |
| JP | 2009504283 A | 2/2009 |
| JP | 2009504898 A | 2/2009 |
| JP | 2009504897 A | 5/2009 |
| JP | 2010523805 A | 7/2010 |
| JP | 2012143575 A | 8/2012 |
| JP | 2015097814 A | 5/2015 |
| KR | 20090035724 A | 4/2009 |
| WO | WO-8900755 A1 | 1/1989 |
| WO | WO-9729793 A1 | 8/1997 |
| WO | WO-9801085 A1 | 1/1998 |
| WO | WO-9814223 A1 | 4/1998 |
| WO | WO-0049079 A1 | 8/2000 |
| WO | WO-0105337 A1 | 1/2001 |
| WO | WO-0180778 A1 | 11/2001 |
| WO | WO-03049930 A1 | 6/2003 |
| WO | WO-2004024204 A1 | 3/2004 |
| WO | WO-2004064618 A2 | 8/2004 |
| WO | WO-2004064618 A3 | 8/2004 |
| WO | WO-2004101009 A1 | 11/2004 |
| WO | WO-2006041969 A1 | 4/2006 |
| WO | WO-2007019874 A1 | 2/2007 |
| WO | WO-2007024684 A2 | 3/2007 |
| WO | WO-2007024686 A3 | 3/2007 |

(56) References Cited

FOREIGN PATENT DOCUMENTS

| WO | WO-2007056561 A2 | 5/2007 |
|---|---|---|
| WO | WO-2007121167 A1 | 10/2007 |
| WO | WO-2008016174 A1 | 2/2008 |
| WO | WO-2008052574 A1 | 5/2008 |
| WO | WO-2008092047 A1 | 7/2008 |
| WO | WO-2008101073 A2 | 8/2008 |
| WO | WO-2008101134 A1 | 8/2008 |
| WO | WO-2008113388 A1 | 9/2008 |
| WO | WO-2008124825 A2 | 10/2008 |
| WO | WO-2009032909 A2 | 3/2009 |
| WO | WO-2009045658 A1 | 4/2009 |
| WO | WO-2009032909 A3 | 12/2009 |
| WO | WO-2010129514 A2 | 11/2010 |
| WO | WO-2010129514 A3 | 11/2010 |

OTHER PUBLICATIONS

US 7,253,214, 8/2007, McKellop, Harry A, et al. (withdrawn).

"U.S. Appl. No. 11/465,743, Advisory Action mailed Jul. 16, 2008", 5 pgs.

"U.S. Appl. No. 11/465,743, Advisory Action mailed Aug. 6, 2008", 6 pgs.

"U.S. Appl. No. 11/465,743, Advisory Action rnailed Aug. 24, 2009", 6 pgs.

"U.S. Appl. No. 11/465,743, Amended Appeal Brief filed Mar. 10, 2010", 42 pgs.

"U.S. Appl. No. 11/465,743, Amended Appeal Brief filed Dec. 15, 2009", 41 pgs.

"U.S. Appl. No. 11/465,743, Appeal Brief filed Nov. 15, 2009", 41 pgs.

"U.S. Appl. No. 11/465,743, Examiner Interview Summary mailed Apr. 29, 2009", 4 pgs.

"U.S. Appl. No. 11/465,743, Examiner Interview Summary mailed Sep. 23, 2010", 2 pgs.

"U.S. Appl. No. 11/465,743, Examiner Interview Summary mailed Sep. 29, 2010", 2 pgs.

"U.S. Appl. No. 11/465,743, Examiner Interview Summary mailed Oct. 31, 2008", 3 pgs.

"U.S. Appl. No. 11/465,743, Final Office Action mailed May 1, 2008", 9 pgs.

"U.S. Appl. No. 11/465,743, Final Office Action mailed Jun. 16, 2009", 11 pgs.

"U.S. Appl. No. 11/465,743, Non Final Office Action mailed Sep. 28, 2007", 7 pgs.

"U.S. Appl. No. 11/465,743, Non Final Office Action mailed Dec. 15, 2008", 12 pgs.

"U.S. Appl. No. 11/465,743, Notice of Allowance mailed May 26, 2010", 6 pgs.

"U.S. Appl. No. 11/465,743, Notice of Allowance mailed Sep. 3, 2010", 7 pgs.

"U.S. Appl. No. 11/465,743, Response filed Jan. 17, 2008 to Non Final Office Action mailed Sep. 28, 2007", 13 pgs.

"U.S. Appl. No. 11/465,743, Response filed Mar. 16, 2009 to Non Final Office Action mailed Dec. 15, 2008", 11 pgs.

"U.S. Appl. No. 11/465,743, Response filed Jul. 1, 2008 to Final Office Action mailed May 1, 2008", 8 pgs.

"U.S. Appl. No. 11/465,743, Response filed Jul. 22, 2008 to Advisory Action mailed Jul. 16, 2008", 6 pgs.

"U.S. Appl. No. 11/465,743, Response filed Jul. 29, 2009 to Final Office Action mailed Jun. 16, 2009", 15 pgs.

"U.S. Appl. No. 11/465,743, Response filed Oct. 31, 2008 to Advisory Action mailed Aug. 6, 2008", 15 pgs.

"U.S. Appl. No. 11/465,743, Supplemental Notice of Allowability mailed Jul. 14, 2010", 2 pgs.

"U.S. Appl. No. 11/465,743, Supplemental Notice of Allowability mailed Sep. 23, 2010", 4 pgs.

"U.S. Appl. No. 11/465,743, Supplemental Notice of Allowability mailed Sep. 29, 2010", 4 pgs.

"U.S. Appl. No. 11/465,743, Supplemental Response filed Apr. 20, 2009 to Non Final Office Action mailed Dec. 15, 2008", 10 pgs.

"U.S. Appl. No. 12/100,894, Examiner Interview Summary mailed Dec. 2, 2009", 3 pgs.

"U.S. Appl. No. 12/100,894, Non Final Office Action mailed Apr. 14, 2009", 16 pgs.

"U.S. Appl. No. 12/100,894, Response filed Mar. 31, 2009 to Restriction Requirement mailed Mar. 2, 2009", 2 pgs.

"U.S. Appl. No. 12/100,894, Restriction Requirement mailed Mar. 2, 2009", 7 pgs.

"U.S. Appl. No. 12/262,531, Final Office Action mailed Jan. 14, 2010", 11 pgs.

"U.S. Appl. No. 12/262,531, Non Final Office Action mailed Jun. 17, 2010", 16 pgs.

"U.S. Appl. No. 12/262,531, Non Final Office Action mailed Jun. 25, 2009", 7 pgs.

"U.S. Appl. No. 12/262,531, Notice of Allowance mailed Oct. 28, 2010", 6 pgs.

"U.S. Appl. No. 12/262,531, Preliminary Amendment filed Oct. 31, 2008", 6 pgs.

"U.S. Appl. No. 12/262,531, Response filed Apr. 28, 2010 to Final Office Action mailed Jan. 14, 2010", 15 pgs.

"U.S. Appl. No. 12/262,531, Response filed Sep. 17, 2010 to Non Final Office Action mailed Jun. 17, 2010", 4 pgs.

"U.S. Appl. No. 12/262,531, Response filed Sep. 23, 2009 to Non Final Office Action mailed Jun. 25, 2009", 10 pgs.

"U.S. Appl. No. 12/262,531, Supplemental Notice of Allowability mailed Nov. 23, 2010", 4 pgs.

"U.S. Appl. No. 12/464,235, Final Office Action mailed Aug. 19, 2010", 11 pgs.

"U.S. Appl. No. 12/464,235, Non Final Office Action mailed Mar. 2, 2010", 7 pgs.

"U.S. Appl. No. 12/464,235, Non Final Office Action mailed Dec. 23, 2010", 10 pgs.

"U.S. Appl. No. 12/579,094, Examiner Interview Summary mailed Jan. 6, 2012", 1 pg.

"U.S. Appl. No. 12/579,094, Final Office Action mailed Oct. 13, 2010", 14 pgs.

"U.S. Appl. No. 12/579,094, Non Final Office Action mailed May 18, 2010", 19 pgs.

"U.S. Appl. No. 12/579,094, Notice of Allowance mailed Jan. 6, 2012", 8 pgs.

"U.S. Appl. No. 12/579,094, Preliminary Amendment filed Oct. 14, 2009", 11 pgs.

"U.S. Appl. No. 12/579,094, Response filed Jan. 27, 2012 to Notice of Allowance mailed Jan. 6, 2012", 5 pgs.

"U.S. Appl. No. 12/579,094, Response filed Jan. 31, 2012 to 312 Amendment mailed Jan. 27, 2012", 2 pgs.

"U.S. Appl. No. 12/579,094, Response filed Apr. 7, 2010 to Restriction Requirement mailed Mar. 9, 2010", 9 pgs.

"U.S. Appl. No. 12/579,094, Response filed Apr. 12, 2011 to Final Office Action mailed Oct. 13, 2010", 45 pgs.

"U.S. Appl. No. 12/579,094, Response filed Sep. 20, 2010 to Non Final Office Action mailed May 18, 2010", 30 pgs.

"U.S. Appl. No. 12/579,094, Restriction Requirement mailed Mar. 9, 2010", 7 pgs.

"U.S. Appl. No. 12/847,741, Examiner interview Summary mailed Aug. 6, 2013", 4 pgs.

"U.S. Appl. No. 12/847,741, Final Office Action mailed Jun. 27, 2012", 7 pgs.

"U.S. Appl. No. 12/847,741, Non Final Office Action mailed Feb. 24, 2012", 11 pgs.

"U.S. Appl. No. 12/847,741, Non Final Office Action mailed May 9, 2013", 11 pgs.

"U.S. Appl. No. 12/847,741, Notice of Allowance mailed Oct. 17, 2013", 11 pgs.

"U.S. Appl. No. 12/847,741, Preliminary Amendment filed Oct. 18, 2010", 5 pgs.

"U.S. Appl. No. 12/847,741, Response filed May 23, 2012 to Non Final Office Action mailed Feb. 24, 2012", 10 pgs.

"U.S. Appl. No. 12/847,741, Response filed Sep. 3, 2013 to Non Final Office Action mailed May 9, 2013", 18 pgs.

"U.S. Appl. No. 12/847,741, Response filed Sep. 26, 2012 to Final Office Action mailed Jun. 27, 2012", 14 pgs.

(56) References Cited

OTHER PUBLICATIONS

"U.S. Appl. No. 12/847,741, Second Preliminary Amendment filed Feb. 21, 2012", 4 pgs.
"U.S. Appl. No. 12/942,703, Applicant's Summary of Examiner Interview filed Feb. 17, 2012", 3 pgs.
"U.S. Appl. No. 12/942,703, Final Office Action mailed Jan. 7, 2013", 8 pgs.
"U.S. Appl. No. 12/942,703, Final Office Action mailed Mar. 16, 2012", 14 pgs.
"U.S. Appl. No. 12/942,703, Non Final Office Action mailed Aug. 2, 2011", 17 pgs.
"U.S. Appl. No. 12/942,703, Non Final Office Action mailed Aug. 23, 2012", 14 pgs.
"U.S. Appl. No. 12/942,703, Notice of Allowance mailed Mar. 1, 2013", 8 pgs.
"U.S. Appl. No. 12/942,703, Response filed Jan. 3, 2012 to Non Final Office Action mailed Aug. 2, 2011", 34 pgs.
"U.S. Appl. No. 12/942,703, Response filed Feb. 13, 2013 to Final Office Action mailed Jan. 7, 2013", 7 pgs.
"U.S. Appl. No. 12/942,703, Response filed Jul. 16, 2012 to Final Office Action mailed Mar. 16, 2012", 14 pgs.
"U.S. Appl. No. 12/942,703, Response filed Nov. 30, 2012 to Non Final Office Action mailed Aug. 23, 2012", 15 pgs.
"U.S. Appl. No. 12/943,160, Applicant's Summary of Examiner Interview filed Feb. 17, 2012", 2 pgs.
"U.S. Appl. No. 12/943,160, Examiner Interview Summary mailed Feb. 3, 2012", 2 pgs.
"U.S. Appl. No. 12/943,160, Examiner Interview Summary mailed Aug. 15, 2013", 3 pgs.
"U.S. Appl. No. 12/943,160, Final Office Action mailed Sep. 28, 2012", 14 pgs.
"U.S. Appl. No. 12/943,160, Non Final Office Action mailed Mar. 16, 2012", 11 pgs.
"U.S. Appl. No. 12/943,160, Non Final Office Action mailed Jun. 26, 2013", 9 pgs.
"U.S. Appl. No. 12/943,160, Non Final Office Action mailed Aug. 12, 2011", 8 pgs.
"U.S. Appl. No. 12/943,160, Notice of Allowance mailed Oct. 17, 2013", 9 pgs.
"U.S. Appl. No. 12/943,160, Response filed Jan. 11, 2012 to Non Final Office Action mailed Aug. 12, 2011", 13 pgs.
"U.S. Appl. No. 12/943,160, Response filed Jul. 16, 2012 to Non Final Office Action mailed Mar. 16, 2012", 13 pgs.
"U.S. Appl. No. 12/943,160, Response filed Sep. 18, 2013 to Non Final Office Action mailed Jun. 26, 2013", 8 pgs.
"U.S. Appl. No. 12/943,160, Response filed Nov. 20, 2012 to Non Final Office Action mailed Sep. 28, 2012", 10 pgs.
"U.S. Appl. No. 12/967,581, Examiner Interview Summary mailed Jan. 23, 2012", 2 pgs.
"U.S. Appl. No. 12/967,581, Notice of Allowance mailed Feb. 7, 2012", 10 pgs.
"U.S. Appl. No. 12/967,581, Preliminary Amendment filed Jan. 19, 2012", 7 pgs.
"U.S. Appl. No. 12/967,581, Preliminary Amendment filed Jan. 27, 2012", 4 pgs.
"U.S. Appl. No. 12/967,581, Preliminary Amendment filed Feb. 18, 2011", 5 pgs.
"U.S. Appl. No. 12/967,581, Preliminary Amendment filed Dec. 14, 2010", 7 pgs.
"U.S. Appl. No. 13/403,040, Advisory Action mailed Jan. 28, 2013", 6 pgs.
"U.S. Appl. No. 13/403,040, Examiner Interview Summary mailed Jan. 30, 2013", 3 pgs.
"U.S. Appl. No. 13/403,040, Final Office Action mailed Nov. 19, 2012", 14 pgs.
"U.S. Appl. No. 13/403,040, Non Final Office Action mailed Jul. 1, 2013", 8 pgs.
"U.S. Appl. No. 13/403,040, Non Final Office Action mailed Jul. 16, 2012", 14 pgs.
"U.S. Appl. No. 13/403,040, Notice of Allowance mailed Oct. 16, 2013", 10 pgs.
"U.S. Appl. No. 13/403,040, Response filed Jan. 22, 2013 to Final Office Action mailed Nov. 19, 2012", 13 pgs.
"Application U.S. Appl. No. 13/403,040, Response filed Feb. 18, 2013 to Advisory Action mailed Jan. 28, 2013", 13 pgs.
"U.S. Appl. No. 13/403,040, Response filed Sep. 3, 2013 to Non Final Office Action mailed Jul. 1, 2013", 13 pgs.
"U.S. Appl. No. 13/403,040, Response filed Oct. 16, 2012 to Non Final Office Action mailed Jul. 16, 2012", 15 pgs.
"Australian Application Serial No. 2005335669, Office Action mailed Mar. 21, 2011", 3 pgs.
"Australian Application Serial No. 2005335669, Response filed Feb. 1, 2012 to Office Action mailed Mar. 21, 2011", 15 pgs.
"Australian Application Serial No. 2008236996, Office Action mailed Jun. 19, 2012", 3 pgs.
"Australian Application Serial No. 2012203503, First Examiner Report mailed May 7, 2013", 4 pgs.
"Australian Application Serial No. 2012203503, Response filed Sep. 24, 2013 to First Examiner Report mailed May 7, 2013", 17 pgs.
"Biomet Orthopedics", Brochure E-POL Y HSLPE (EXH20), (2007), 23 pgs.
"Canadian Application No. 2,619,502, Office Action mailed Nov. 4, 2011", 4 pgs.
"Canadian Application No. 2,619,502, Response filed Jan. 30, 2012 to Office Action mailed Nov. 4, 2011", 6 pgs.
"Canadian Application No. 2,619,502, Response filed Sep. 2, 2011 to Office Action mailed Nov. 4, 2011", 17 pgs.
"Canadian Application Serial No. 2,678,459, Office Action mailed Apr. 11, 2013", 4 pgs.
"Canadian Application Serial No. 2,678,459, Response filed Oct. 11, 2013 to Office Action mailed Apr. 11, 2013", 45 pgs.
"Canadian Application Serial No, 2,788,687, Office Action mailed Jul. 10, 2013", 4 pgs.
"E-POLY HXLPE Brochure", Biomet Orthopedics, (2007), 23 pgs.
"European Application Serial No. 05777319.4, Office Action mailed Jun. 10, 2009", 4 pgs.
"European Application Serial No. 05777319.4, Office Action mailed Jul. 28, 2010", 1 pg.
"European Application Serial No. 05777319.4, Office Action mailed Sep. 15, 2008", 1 pg.
"European Application Serial No. 05777319.4, Response filed Jan. 20, 2009 to Office Action mailed Sep. 15, 2008", 7 pgs.
"European Application Serial No. 05777319.4, Response filed Oct. 8, 2009 to Office Action mailed Jun. 10, 2009", 9 pgs.
"European Application Serial No. 08745507.7, Office Action mailed Jan. 12, 2010", 2 pgs.
"European Application Serial No. 08745507.7, Office Action mailed May 10, 2010", 3 pgs.
"European Application Serial No. 08745507.7, Office Action mailed Jul. 20, 2011", 4 pgs.
"European Application Serial No. 08745507.7, Office Action mailed Dec. 12, 2012", 1 pg.
"European Application Serial No. 08745507.7, Response filed Feb. 16, 2010 to Office Action mailed Jan. 12, 2010", 5 pgs.
"European Application Serial No. 08745507.7, Response filed Sep. 20, 2010 to Office Action mailed May 10, 2010", 3 pgs.
"European Application Serial No. 08745507.7, Response filed Nov. 21, 2011 to Office Action mailed Jul. 20, 2011", 3 pgs.
"European Application Serial No. 09013154.1, European Examination Notification mailed Jan. 4, 2013", 4 pgs.
"European Application Serial No. 09013154.1, European Search Report mailed Feb. 23, 2010", 6 pgs.
"European Application Serial No. 09013154.1, Office Action mailed Sep. 14, 2011", 4 pgs.
"European Application Serial No. 09013154.1, Office Action mailed Oct. 21, 2010", 1 pg.
"European Application Serial No. 09013154.1, Response filed Jan. 26, 2012 to Office Action mailed Sep. 14, 2011", 7 pgs.
"European Application Serial No. 09013154.1, Response filed Mar. 21, 2011 to Office Action mailed Oct. 21, 2010", 22 pgs.

(56) References Cited

OTHER PUBLICATIONS

"European Application Serial No. 09013154.1, Response filed May 14, 2013 to Examination Notification Art, 94(3) mailed Jan. 4, 2013", 9 pgs.
"European Application Serial No. 10012579.8, European Search Report and Written Opinion mailed Feb. 23, 2010", 3 pgs.
"European Application Serial No. 10012579.8, Extended Search Report and Written Opinion mailed Dec. 9, 2010", 8 pgs.
"European Application Serial No. 10012579.8, Office Action mailed Jan. 31, 2011", 2 pgs.
"European Application Serial No. 10012579.8, Office Action mailed Apr. 23, 2012", 4 pgs.
"European Application Serial No. 10012579.8, Office Action mailed Sep. 14, 2011", 4 pgs.
"European Application Serial No. 10012579.8, Office Action mailed Sep. 18, 2012", 4 pgs.
"European Application Serial No. 10012579.8, Response filed Jan. 26, 2012 to Office Action mailed Sep. 14, 2011", 11 pgs.
"European Application Serial No. 10012579.8, Response filed Jan. 28, 2013 to Examination Notification Art, 94(3) mailed Sep. 18, 2012", 9 pgs.
"European Application Serial No. 10012579.8, Response filed Jul. 3, 2012 to Office Action mailed Apr. 23, 2012", 15 pgs.
"European Application Serial No. 10012579.8, Response filed Jul. 26, 2011 to Office Action mailed Jan. 31, 2011", 29 pgs.
"European Application Serial No. 10012589.7, European Search Report mailed Feb. 23, 2010", 6 pgs.
"European Application Serial No. 10012589.7, European Search Report mailed Dec. 9, 2010", 7 pgs.
"European Application Serial No. 10012589.7, Office Action mailed Jan. 31, 2011", 2 pgs.
"European Application Serial No. 10012589.7, Office Action mailed Feb. 3, 2010", 1 pg.
"European Application Serial No. 10012589.7, Office Action mailed Mar. 27, 2012", 4 pgs.
"European Application Serial No. 10012589.7, Office Action mailed Dec. 16, 2010", 1 pg.
"European Application Serial No. 10012589.7, Response filed Jan. 13, 2012", 8 pgs.
"European Application Serial No. 10012589.7, Response filed Feb. 13, 2012 to Office Action mailed Dec. 2, 2011", 7 pgs.
"European Application Serial No. 10012589.7, Response filed Jul. 26, 2011 to Office Action mailed Jan. 31, 2011", 9 pgs.
"European Application Serial No. 12154330.0, European Search Report mailed Jul. 18, 2012", 15 pgs.
"European Application Serial No. 12154330.0, Examination Notification Art. 94(3) mailed May 30, 2013", 11 pgs.
"European Application Serial No. 12154330.0, Examination Notification Art. 94(3) mailed Aug. 7, 2013", 9 pgs.
"European Application Serial No. 12154330.0, Response filed Feb. 15, 2013 to Extended European Search Report mailed Jul. 18, 2012", 18 pgs.
"European Application Serial No. 12154330.0, Response filed Jul. 3, 2013 to Examination Notification Art, 94(3) mailed May 30, 2013", 8 pgs.
"European Application Serial No. 12167580.5, Extended European Search Report mailed Feb. 4, 2013", 15 pgs.
"European Application Serial No. 12167580.5, Response filed Sep. 5, 2013 to Extended European Search Report mailed Apr. 4, 2013", 18 pgs.
"European Application Serial No. 12167581.3, European Search Report mailed Mar. 13, 2013", 13 pgs.
"European Application Serial No. 12167581.3, Response filed Oct. 10, 2013 to Extended European Search Report mailed Mar. 13, 2013", 16 pgs.
"International Application Serial No. PCT/EP2005/008967, International Preliminary Report on Patentability mailed Feb. 20, 2008", 7 pgs.
"International Application Serial No. PCT/EP2005/008967, International Search Report and Written Opinion mailed Jun. 21, 2006", 10 pgs.
"International Application Serial No. PCT/EP2009/008250, International Search Report mailed Jan. 21, 2010", 3 pgs.
"International Application Serial No. PCT/EP2009/008250, Written Opinion mailed Jan. 21, 2010", 5 pgs.
"International Application Serial No. PCT/US2008/059909, International Preliminary Report on Patentability mailed Nov. 10, 2009", 8 pgs.
"International Application Serial No. PCT/US2008/059909, International Search Report and Written Opinion mailed Sep. 14, 2009", 14 pgs.
"International Application Serial No. PCT/US2008/086817, International Search Report mailed Sep. 14, 2009", 3 pgs.
"International Application Serial No. PCT/US2008/086817, Written Opinion mailed Sep. 14, 2009", 7 pgs.
"International Application Serial No. PCT/US2009/032412, International Search Report and Written Opinion mailed Mar. 25, 2010", 9 pgs.
"Japanese Application Serial No. 2008-526378, Office Action mailed Jun. 19, 2012", (w/ English translation), 6 pgs.
"Japanese Application Serial No. 2008-526378, Office Action mailed Sep. 6, 2011", (w/ English Translation), 11 pgs.
"Japanese Application Serial No. 2008-526378, Office Action mailed Dec. 18, 2012", (w/ English translation), 4 pgs.
"Japanese Application Serial No. 2008-526378, Response filed Mar. 6, 2012 to Office Action mailed Sep. 6, 2011", (w/ English translation of claims), 10 pgs.
"Japanese Application Serial No. 2008-526378, Response filed May 28, 2013 to Office Action mailed Dec. 18, 2012", (w/ English translation of claims), 8 pgs.
"Japanese Application Serial No. 2008-526378, Response filed Oct. 19, 2012 to Examiners Decision of Final Refusal mailed Jun. 19, 2012", (w/ English translation of claims), 13 pgs.
"Japanese Application Serial No. 2010-503206, Examiners Decision of Final Refusal mailed May 7, 2013", (w/ English translation), 5 pgs.
"Japanese Application Serial No. 2010-503206, Office Action mailed Dec. 4, 2012", (w/ English translation), 7 pgs.
"Japanese Application Serial No. 2010-503206, Response filed Mar. 4, 2013 to Office Action mailed Dec. 4, 2012", (w/ English translation), 13 pgs.
"Japanese Application Serial No. 2012-049675, Office Action mailed Sep. 3, 2013", (w/ English translation), 13 pgs.
"Joint Replacement Material Developed at the Massachusetts General Hospital", from MA General Hosp. MGH Hotline On-line publication, (Aug. 10, 2007), 1 pg.
"New joint replacement material developed at Massachusetts General Hospital and put to first clinic use", news release from Massachusetts General Hospital, accessed May 13, 2008, (Nov. 15, 2010), 2 pgs.
"Prevention of Fatigue Cracks in Ultrahigh Morecular Weight Polyethylene joint Components by the Addition of Vitamin E", J. Biomed, Mater. Res., vol. 48 (1999), 474-478.
"Studies on the effect of electron beam radiation on the molecular structure of ultra-high molecularweight polyethylene under the influence of a-tocopherol with respect to its application in medical implants", J. Materials Science: Materials in Medicine, vol. 13, No. 10, (2002), 917-921.
"The anti-oxidative properties of a-tocopherol in y-irradiated UHMWPE with respect to fatigue and oxidation resistance", Biomatyerials, vol. 26, (Apr. 1, 2005), 5755-5762.
Bragdon, et al., "A New Pin-on-disk wear testing method for simulating wear of polyethylene on cobalt-chrome alloy in total hip arthroplasty", The Journal of Arthoplasty vol. 16, No. 5, (2001), 658-665.
Greer, K. W., et al., "The Effects of Raw Material, Irradiation Dose, and Irradiation Source on Crosslinking of UHMWPE", Journal of ASTM International, vol. 1, No. 1, (Jan. 2004), pp. 1-11.
Kurtz, S, et al., "Trace Concentrations of Vitamin E Protect Radiation Crosslinked UHMWPE from Oxidative Degradation", 53rd Annual Meeting of the Orthopaedic Research Society, Feb. Paper No. 0020, (Nov. 14, 2007), 1 pg.

(56) References Cited

OTHER PUBLICATIONS

Oral, et al., "Alpha-Tocopherol-doped irradiated UHMWPE for high fatigue resistance and low wear", Biomaterials vol. 25, (2004), 5515-5522.
Oral, et al., "Blending a-Tocopherol with UHMWPE Powder for Oxidation Resistance", Poster 1485, 50th Annual Meeting of Orthopaedic Research Society, San Francisco CA, Mar. 7-10, 2004, Transactions, vol. 29, (2004), 1 pg.
Oral. E, et al., "Characterization of irradiated blends of alpha-tocopherol and UHMWPE", Biomaterials, 26(33), (Nov. 2005), 6657-6663.
Oral, E, et al,, "Crosslinked Vitamin E Blended UHMWPE with Improved Grafting and Wear Resistance", ORS Annual Meeting, Poster No. 1131, (2011), 1 pg.
Oral, E, et al, "Trace amounts of grafted vitamin E protect UHMWPE against squalene-initiated oxidation", ORS Annual Meeting, Poster No. 1295, (2011), 1 pg.
Parth, M., et al., "Studies on the effect of electron beam radiation on the molecular structure of ultra-high molecular weight polyethylene under the influence of a-tocopherol with respect to its application in medical implants", Journal of Materials Science: Materials in Medicine, 13(10), (2002), 917-921.
Pletcher. Dirk, et al., "Polymers Compositions Including an Antioxidant", U.S. Appl. No. 12/813,401, filed Jun. 10, 2010, 52 pgs.
Rowell, S, et al., "Detection of Vitamin E in Irradiated UHMWPE by UV-Visible Spectroscopy", ORS 2011 Annual Meeting, Poster No. 1186, (2011), 1 pg.
Rufner, Alicia, et al., "An Antioxidant Stabilized Crosslinked Ultra-High Molecular Weight Polyethylene for Medical Device Applications", U.S. Appl. No. 12/847,741, filed Jul. 30, 2010, 69 pgs.
Shibata. N, et al., "The anti-oxidative properties of alpha-tocopherol in gamma-irradiated UHMWPE with respect to fatigue and oxidation resistance", Biomaterials, 26(29), (Oct. 2005), 5755-5762.
Tomita, N., et al., "Prevention of fatigue cracks in ultrahigh molecular weight polyethylene joint components by the addition of vitamin E", J Biomed Mater Res., 48(4), (1999), 474-8.
Wannomae, et al., "Vitamin E Stabilized, Irradiated UHMWPE for Cruciate Retaining Knee Components", 53rd Annual Meeting of the Orthopaedic Research Society, Poster No. 1783, (Nov. 14, 2007), 1 pg.
Wolf. C. et al., "Radiation Grafting of Vitamin E to Ultra High Molecular Weight Polyethylene", ORS Annual Meeting, Poster No. 1178, (2011), 1 pg.
"U.S. Appl. No. 13/403,040, PTO Response to 312 Amendment mailed Feb. 6, 2014", 2 pgs.
"U.S. Appl. No. 14/157,687, Preliminary Amendment mailed Jan. 22, 2014", 6 pgs.
"U.S. Appl. No. 14/157,695, Preliminary Amendment filed Jan. 29, 2014", 21 pages.
"Australian Application Serial No. 2013200780, First Examiner Report mailed May 3, 2014", 3 pgs.
"Australian Application Serial No. 2013200780, Response filed Apr. 9, 2014 to First Examiner Report mailed Jan. 3, 2014", 28 pgs.
"Australian Application Serial No. 2013200780, Response filed Aug. 5, 2014 to Office Action mailed May 22, 2014", 3 pgs.
"Australian Application Serial No. 2013200780, Subsequent Examiners Report mailed May 22, 2014", 3 pgs.
"Australian Application Serial No. 2013200780, Subsequent Examiners Report mailed Sep. 3, 2014", 3 pgs.
"Canadian Application Serial No. 2,788,687, Office Action mailed Jun. 4, 2014", 2 pgs.
"Canadian Application Serial No. 2,788,687, Response filed Jul. 10, 2013 to Office Action mailed Jan. 10, 2014", 25 pgs.
"European Application Serial No. 10012579.8, Notice of Opposition mailed Aug. 18, 2014", 1 pg.
"European Application Serial No. 12154330.0, Response filed Dec. 17, 2013 to Examination Notification Art. 94(3) mailed Aug. 7, 2013", 14 pgs.
"European Application Serial No. 14173530.8, Extended European Search Report mailed Sep. 24, 2014", 8 pgs.
"Japanese Application Serial No. 2012-049675, Examiners Decision of Final Refusal mailed Sep. 30, 2014", 9 pgs.
"Japanese Application Serial No. 2012-049675, Response filed Feb. 28, 2014 to Office Action mailed Sep. 3, 2013", 14 pgs.
Ingo, John, "Evaluation of cross-linked UHMWPE with regards to its suitability as implant material for hip joint shells", Series: Plastics Research published by Manfred H. Wagner, Translation, (2003), 28 pgs.
Muratoglu, Orhun K, et al., "Larger Diameter Femoral Heads Used in Conjunction With a Highly Cross-Linked Ultra-High Molecular Weight Polyethylene: A New Concept", The Journal of Arthoplasty 16(8) Suppl. 1, (2001), 24-30.
"U.S. Appl. No. 14/157,695, Final Office Action mailed Sep. 2, 2015", 13 pgs.
"U.S. Appl. No. 14/157,695, Non Final Office Action mailed May 8, 2015", 16 pgs.
"U.S. Appl. No. 14/157,695, Response filed Aug. 7, 2015 to Non Final Office Action mailed May 8, 2015", 18 pgs.
"Canadian Application Serial No. 2,678,459, Office Action mailed Nov. 21, 2014", 2 pgs.
"European Application Serial No. 12154330.0, Examination Notification Art. 94(3) mailed Mar. 10, 2015", 10 pgs.
"European Application Serial No. 12167580.5, Examination Notification Art. 94(3) mailed Mar. 26, 2015", 3 pgs.
"European Application Serial No. 12167581.3, Examination Notification Art. 94(3) mailed Mar. 26, 2015", 4 pgs.
"International Application Serial No. PCT/US2015/017741, International Search Report mailed Aug. 7, 2015", 5 pgs.
"International Application Serial No. PCT/US2015/017741, Written Opinion mailed Aug. 7, 2015", 7 pgs.
"Japanese Application Serial No. 2015-016315, Amendment filed Feb. 26, 2015", (W/ English Translation), 8 pgs.
"JP 11-239611A, English Translation", 10 pgs.
"Opposition Application No. 09013154.1, Opposition Brief filed Apr. 16, 2014", (w/ English Translation), 22 pgs.
"Opposition to EP 2277560, Notice of Opposition filed on Jul. 4, 2014", 14 pgs.
"Opposition to EP 2277560, Response filed Feb. 26, 2015 to Notice of Opposition filed on Jul. 4, 2014", 12 pgs.
Davidson, Ernesto, et al., "Characterization of UHMWPE Irradiated with gamma rays stored in E vitamin and thermally treated", Revista De La Facultad De Ingenieria Universidad Central De Venezuela, 26(1) (2011), 7 pgs.
Muratoglu, Orhun K., et al., "A Novel Method of Cross-Linking Ultra-High-MolecularWeight Polyethylene to Improve Wear, Reduce Oxidation, and Retain Mechanical Properties", The Journal of Arthroplasty, vol. 16, No. 2, (2001), 149-160.

\* cited by examiner

ANTIOXIDANT STABILIZED CROSSLINKED ULTRA-HIGH MOLECULAR WEIGHT POLYETHYLENE FOR MEDICAL DEVICE APPLICATIONS

CROSS-REFERENCE TO RELATED APPLICATIONS

This application is a Continuation of U.S. patent application Ser. No. 13/403,040, which is a Continuation of U.S. patent application Ser. No. 12/579,094, entitled AN ANTIOXIDANT STABILIZED CROSSLINKED ULTRA-HIGH MOLECULAR WEIGHT POLYETHYLENE FOR MEDICAL DEVICE APPLICATIONS, filed Oct. 14, 2009, now issued as U.S. Pat. No. 8,129,440, which is a Continuation of U.S. patent application Ser. No. 12/100,894, entitled AN ANTIOXIDANT STABILIZED CROSSLINKED ULTRA-HIGH MOLECULAR WEIGHT POLYETHYLENE FOR MEDICAL DEVICE APPLICATIONS, filed Apr. 10, 2008, now abandoned, which claims priority to U.S. Provisional Patent Application Ser. No. 60/922,738, entitled AN ANTIOXIDANT STABILIZED CROSSLINKED ULTRA-HIGH MOLECULAR WEIGHT POLYETHYLENE FOR MEDICAL DEVICE APPLICATIONS, filed on Apr. 10, 2007, the entire disclosures of which are expressly incorporated by reference herein.

BACKGROUND

1. Field of the Invention

The present invention relates to crosslinked ultra-high molecular weight polyethylene and, particularly, to antioxidant stabilized, crosslinked ultra-high molecular weight polyethylene.

2. Description of the Related Art

Ultra-high molecular weight polyethylene (UHMWPE) is commonly utilized in medical device applications. In order to beneficially alter the material properties of UHMWPE and decrease its wear rate, UHMWPE may be crosslinked. For example, UHMWPE may be subjected to electron beam irradiation, gamma irradiation, or x-ray irradiation, causing chain scissions of the individual polyethylene molecules as well as the breaking of C—H bonds to form free radicals on the polymer chains. While free radicals on adjacent polymer chains may bond together to form crosslinked UHMWPE, some free radicals may remain in the UHMWPE following irradiation, which could potentially combine with oxygen, causing oxidation of the UHMWPE.

Oxidation detrimentally affects the material properties of UHMWPE and may also increase its wear rate. To help eliminate the free radicals that are formed during irradiation and that may continue to exist thereafter, UHMWPE may be melt annealed by heating the crosslinked UHMWPE to a temperature in excess of its melting point. By increasing the temperature of the UHMWPE above its melting point, the mobility of the individual polyethylene molecules is significantly increased, facilitating additional crosslinking of the polyethylene molecules and the quenching of free radicals.

While melt annealing irradiated, crosslinked UHMWPE helps to eliminate free radicals and reduce the potential for later oxidation of the UHMWPE, the melt annealing could potentially reduce other mechanical properties of the UHMWPE.

SUMMARY

The present invention relates to a crosslinked UHMWPE and, particularly, an antioxidant stabilized, crosslinked UHMWPE. In one exemplary embodiment, an antioxidant is combined with UHMWPE prior to subjecting the UHMWPE to crosslinking irradiation. In one exemplary embodiment, the antioxidant is tocopherol. After the antioxidant is combined with the UHMWPE, the resulting blend may be formed into slabs, bar stock, and/or incorporated into a substrate, such as a metal, for example. The resulting product may then be subjected to crosslinking irradiation. In one exemplary embodiment, the UHMWPE blend is preheated prior to subjecting the same to crosslinking irradiation. Once irradiated, the UHMWPE blended product may be machined, packaged, and sterilized in accordance with conventional techniques.

In one exemplary embodiment, the formed UHMWPE/antioxidant blend may be subjected to multiple passes of crosslinking irradiation. By irradiating the blend in multiple passes, the maximum dose of radiation received by the UHMWPE blend at any one time is lessened. As a result, the maximum temperature of the UHMWPE blend reached during irradiation is correspondingly lessened. This allows for the UHMWPE to maintain a higher level of desirable mechanical properties and prevents substantial melting of the UHMWPE. In one exemplary embodiment, the UHMWPE is cooled after each individual pass of crosslinking irradiation. By allowing the UHMWPE blend to cool, the temperature at the time of subsequent irradiation is high enough to encourage the mobility of the individual polyethylene molecules, but is also low enough that the temperature increase experienced during irradiation is unlikely to substantially alter any desired material properties of the UHMWPE blend.

Advantageously, by incorporating an antioxidant, such as tocopherol, into the UHMWPE prior to subjecting the same to crosslinking irradiation, the UHMWPE may be stabilized without the need for post irradiation melt annealing or any other post-irradiation treatment to quench free radicals. Specifically, an antioxidant, such as tocopherol, acts as a free radical scavenger and, in particular, acts as an electron donor to stabilize free radicals. While tocopherol itself then becomes a free radical, tocopherol is a stable, substantially unreactive free radical. Additionally, because of the substantially reduced level of oxidation that occurs using a UHMWPE/antioxidant blend, the amount of oxidized material that must be removed to form a final, implantable medical component is reduced. As a result, the size of the stock material subjected to irradiation may be smaller in dimension, making it easier to handle and easier to manufacture into final medical components.

Moreover, by subjecting the UHMWPE/antioxidant blend to multiple passes of irradiation, the UHMWPE blend may be integrally incorporated onto a substrate prior to irradiation. Specifically, as a result of separating the total radiation dose into a plurality of individual passes, the temperature of the UHMWPE blend at the UHMWPE/substrate interface remains low enough that separation of the UHMWPE blend and the substrate is substantially prevented. Further, even after irradiation, some antioxidant remains unreacted within the UHMWPE blend, which may continue to quench free radicals throughout the lifetime of the medical component. Thus, even after the medical component is implanted, the antioxidant may continue to quench free radicals and further reduce the likelihood of additional oxidation.

In one form thereof, the present invention provides method for processing UHMWPE for use in medical applications, the method including the steps of: combining UHMWPE with an antioxidant to form a blend having 0.01 to 3.0 weight percent of the antioxidant, the UHMWPE having a melting point; processing the blend to consolidate, the consolidated blend having a melting point; preheating the consolidated blend to a preheat temperature below the melting point of the consolidated blend; and irradiating the consolidated blend while maintaining the consolidated blend at a temperature below the melting point of the consolidated blend In another form thereof, the present invention provides a crosslinked UHMWPE blend for use in medical implants prepared by a process including the steps of: combining UHMWPE with an antioxidant to form a blend having 0.1 to 3.0 weight percent antioxidant; processing the blend to consolidate the blend, the consolidated blend having a melting point; preheating the consolidated blend to a preheat temperature below the melting point of the consolidated blend; and irradiating the consolidated blend with a total irradiation dose of at least 100 kGy while maintaining the consolidated blend at a temperature below the melting point of the consolidated blend.

BRIEF DESCRIPTION OF THE DRAWING

The above-mentioned and other features and advantages of this invention, and the manner of attaining them, will become more apparent and the invention itself will be better understood by reference to the following description of an embodiment of the invention taken in conjunction with the accompanying drawings, wherein.

The exemplifications set out herein illustrate embodiments of the invention and such exemplifications are not to be construed as limiting the scope of the invention in any manner.

DETAILED DESCRIPTION

Figure 1:
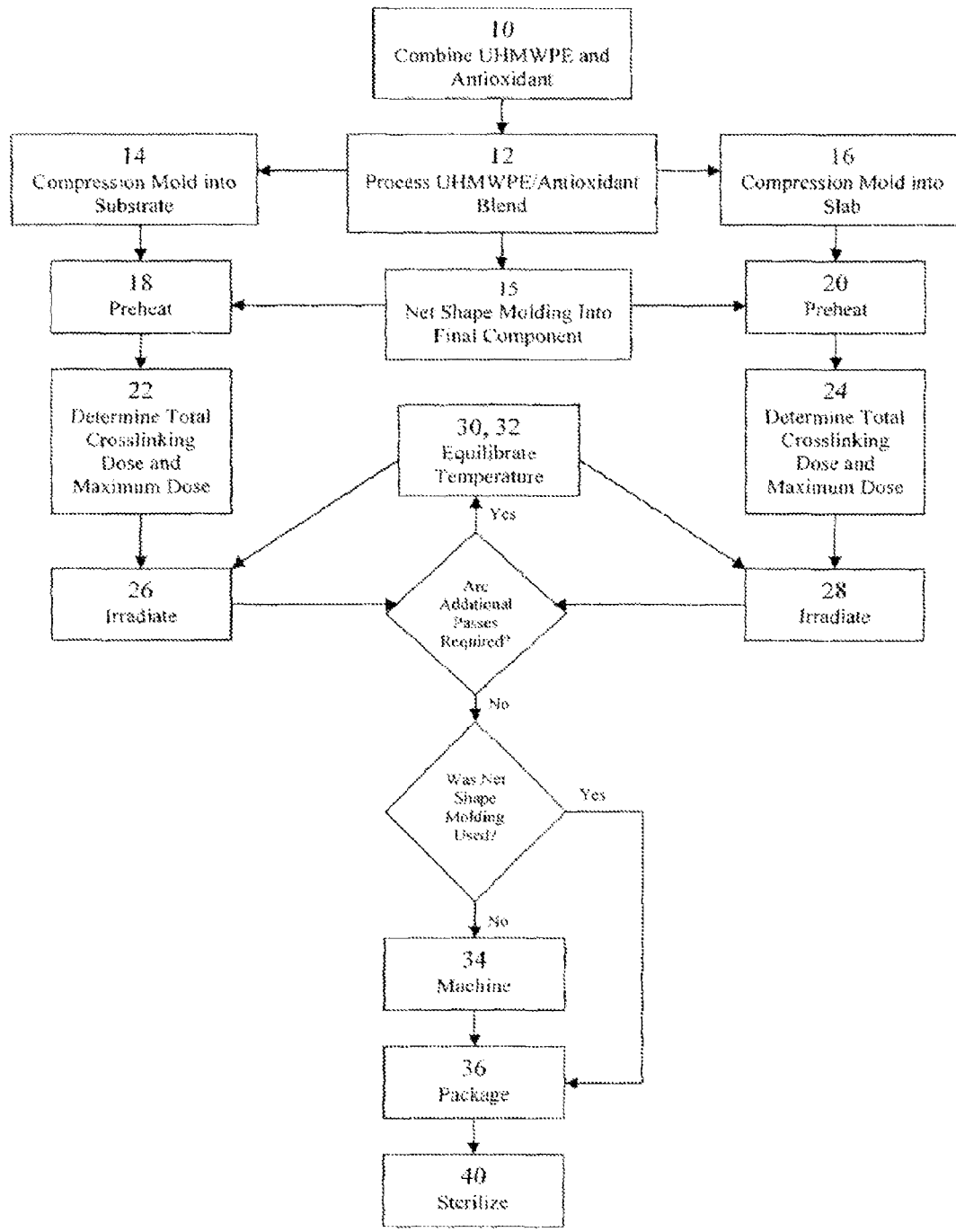
FIG. 1 is schematic depicting exemplary processes for preparing and using the crosslinked UHMWPE blends of the present invention.

Referring to FIG. 1, UHMWPE is combined with an antioxidant to create a UHMWPE/antioxidant blend (the "UHMWPE blend"). Once combined, the UHMWPE blend may be processed to fabricate the same into a desired form. Once formed, the UHMWPE blend may be preheated and subjected to cross-linking irradiation. The crosslinked UHMWPE blend may then be subjected to machining, packaging, and sterilization.

To create the UHMWPE/antioxidant blend, any medical grade UHMWPE powder may be utilized. For example, GUR 1050 and GUR 1020 powders, both commercially available from Ticona, having North American headquarters located in Florence, Ky., may be used. Similarly, while any antioxidant, such as Vitamin C, lycopene, honey, phenolic antioxidants, amine antioxidants, hydroquinone, beta-carotene, ascorbic acid, CoQ-enzyme, and derivatives thereof, may be used, the UHMWPE blend referred to herein is a UHMWPE/tocopherol, i.e., Vitamin E, blend. Additionally, as any tocopherol may be used in conjunction with the present invention, such as d-α-tocopherol, d,l-α-tocopherol, or α-tocopherol acetate, unless otherwise specifically stated herein, the term "tocopherol" in its generic form refers to all tocopherols. However, the synthetic form, d,l-α-tocopherol, is the most commonly used.

In combining UHMWPE and tocopherol, any mechanism and/or process achieving a substantially homogenous blend of the components may be utilized. In one exemplary embodiment, solvent blending is utilized. In solvent blending, tocopherol is mixed with a volatile solvent to lower the viscosity of the tocopherol and facilitate homogenous blending of the tocopherol with the UHMWPE. Once the tocopherol is mixed with the solvent, the tocopherol/solvent mixture may be combined with the UHMWPE, such as with a cone mixer. The solvent is then evaporated, leaving only the UHMWPE/tocopherol blend. In another exemplary embodiment, tocopherol may be blended with UHMWPE by precision coating or atomization. For example, tocopherol may be precision coated onto the UHMWPE powder using a MP-1 MULTI-PROCESSOR™ Fluid Bed connected to a laboratory module Precision Coater available from Niro Inc. of Columbia, Md. MULTI-PROCESSOR™ is a trademark of Niro Inc.

In another exemplary embodiment, low intensity mixing may be used. Low intensity, i.e. low shear, mixing may be performed using a Diosna P100 Granulator, available from Diosna GmbH of Osnabrück, Germany, a subsidiary of Multimixing S.A. In another exemplary embodiment, high shear mixing may be used. High shear mixing of UHMWPE and tocopherol may be achieved using a RV02E or a R05T High Intensity Mixer, both commercially available from Eirich Machines of Gurnee, Ill. Alternatively, high shear mixing may be achieved using a Collette ULTIMAPRO™ 75 One Pot Processor available from Niro, Inc. of Columbia, Md. ULTIMAPRO™ is a trademark of Niro, Inc. Based on the results of testing the above identified methods useful for combining UHMWPE and tocopherol, high shear mixing appears to provide favorable results, including an acceptable homogeneity and a low number of indications, i.e., areas of high tocopherol concentrations relative to the surrounding areas as determined by visual inspection under ultraviolet light or by chemical measurements, such as infrared spectroscopy or gas chromatography. Additionally, in other exemplary embodiments, the fluidized bed, emulsion polymerization, electrostatic precipitation, wetting or coating of particles, and/or master batch blending may be used to combine the UHMWPE and tocopherol.

Irrespective of the method used to combine the UHMWPE and tocopherol to form the UHMWPE blend, the components are combined in ratios necessary to achieve a tocopherol concentration of between 0.01 weight percent (wt. %) and 3 wt. %. In exemplary embodiments, the tocopherol concentration may be as low as 0.01 wt. %, 0.05 wt. %, and 0.1 wt. %, or as high as 0.6 wt. %, 0.8 wt. %, and 1.0 wt. %, for example. In determining the appropriate amount of tocopherol, two competing concerns exist. Specifically, the amount selected must be high enough to quench free radicals in the UHMWPE, but must also be low enough to allow sufficient crosslinking so as to maintain acceptable wear properties of the UHMWPE. In one exemplary embodiment, a range of tocopherol from 0.1 to 0.6 wt. % is used to successfully quench free radicals while still maintaining acceptable wear properties.

Once the UHMWPE blend is substantially homogenously blended and the amount of tocopherol is determined to be within an acceptable range, the UHMWPE blend is processed to consolidate the UHMWPE blend, as indicated at Step 12 of FIG. 1. The UHMWPE blend may be processed by compression molding, net shape molding, injection molding, extrusion, monoblock formation, fiber, melt spinning, blow molding, solution spinning, hot isostatic pressing, high pressure crystallization, and films. In one exemplary embodiment, as indicated at Step 16 of FIG. 1, the UHMWPE blend is compression molded into the form of a slab. In another exemplary embodiment, indicated at Step 14 of FIG. 1, the UHMWPE blend may be compression molded into a substrate, as described in further detail below. For example, the UHMWPE blend may be compression molded into a roughened surface by macroscopic mechanically interlocking the UHMWPE blend with features formed at the roughened surface of the substrate. Similarly, the UHMWPE blend may be molded into another polymer or another antioxidant stabilized polymer. Alternatively, the UHMWPE blend may be net shape molded into the shape of the final orthopedic component at Step 15 of FIG. 1. In this embodiment, if the final orthopedic component includes a substrate, the UHMWPE blend is net shape molded into the substrate at Step 15 and is processed in the same manner as a UHMWPE blend compression molded into a substrate at Step 14, as described in detail below. In contrast, if the UHMWPE blend is net shape molded at Step 15, but is not net shape molded into a substrate, the component is then processed in the same manner as a UHMWPE blend compression molded into a slab at Step 16, as described in detail below.

In one exemplary embodiment, the substrate may be a highly porous biomaterial useful as a bone substitute, cell receptive material, tissue receptive material, an osteoconductive material, and/or an osteoinductive material. A highly porous biomaterial may have a porosity as low as 55, 65, or 75 percent or as high as 80, 85, or 90 percent. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the entire disclosure of which is expressly incorporated herein by reference. In addition to tantalum, all porous coating and other metals such as niobium, tivanium, cancellous structured titanium, or alloys of tantalum and niobium with one another or with other metals may also be used.

After processing, the UHMWPE blend may be heated to a temperature below the melting point of the UHMWPE blend to relieve any residual stresses that may have been formed during processing and to provide additional dimensional stability. In one exemplary embodiment, the melting point of the UHMWPE blend is determined according to standard methods using differential scanning calorimetry. Heating the UHMWPE blend below the melting point creates a more homogenous mixture and increases the final crystallinity. In one exemplary embodiment, the UHMWPE blend is heated to a temperature below its melting point, e.g., between 80° Celsius (C.) and 140° C., and held isothermally for six hours. In other exemplary embodiments, the UHMWPE may be heated to a temperature as low as 80° C., 90° C., 95° C., or 100° C. or as high as 110° C., 115° C., 120° C., and 126° C. In other exemplary embodiments the temperature may be held for as short as 0.5 hours, 1.0 hours, 1.5 hours, or 2.0 hours or as long as 3.0 hours, 4.0 hours, 5.0 hours, or 6.0 hours. In another exemplary embodiment, the UHMWPE blend is heated after irradiation, described below, to provide similar benefits to the UHMWPE blend.

Irrespective of whether the UHMWPE blend is heated to a temperature below the melting point of the UHMWPE blend to relieve any residual stress, the processed UHMWPE blend is preheated at Steps 18, 20 of FIG. 1 in preparation for receiving crosslinking irradiation. In one exemplary embodiment, the processed UHMWPE blend may be preheated to any temperature between room temperature, approximately 23° C., up to the melting point of the UHMWPE blend, approximately 140° C. In another exemplary embodiment, the UHMWPE blend is preheated to a temperature between 60° C. and 130° C. In other exemplary embodiments, the UHMWPE blend may be heated to a temperature as low as 60° C., 70° C., 80° C., 90° C., or 100° C. or as high as 110° C., 120° C., 130° C., 135° C., 140° C. By preheating the processed UHMWPE blend before irradiation, the material properties of the resulting irradiated UHMWPE blend are affected. Thus, the material properties for a UHMWPE blend irradiated at a relatively cold, e.g., approximately 40° C., temperature are substantially different than the material properties for a UHMWPE blend irradiated at a relatively warm, e.g., approximately 120° C. to approximately 140° C., temperature.

However, while the material properties of a UHMWPE blend irradiated at a lower temperature may be superior, the wear properties, fatigue properties, oxidation level, and free radical concentration are all negatively affected. In contrast, while irradiation of a UHMWPE blend at a higher temperature may slightly diminish the material properties, it also results in a higher crosslinking efficiency due to higher chain mobility and adiabatic melting. Additionally, by irradiating at a higher temperature, a greater number of crosslinks are formed. Thus, there are less free radicals in the UHMWPE blend and less tocopherol is consumed by reacting with the free radicals during irradiation and immediately thereafter. As a result, a greater amount of tocopherol remains in the blend that may react with free radicals during the UHMWPE blend's lifecycle, i.e., after irradiation. This, in turn, increases the overall oxidative stability of the UHMWPE blend.

Referring specifically to Step 18, when the UHMWPE blend and its associated substrate are irradiated, the substrate may rapidly increase in temperature. Thus, the temperature increase of the substrate should be taken into account when determining the preheat temperature of the UHMWPE blend and substrate. In one exemplary embodiment, a UHMWPE blend formed to a highly porous substrate manufactured using Trabecular Metal™ technology is preheated to a temperature between 40° C. and 120° C. prior to subjecting the substrate and UHMWPE blend to crosslinking irradiation. A further consideration that may impact the preheat temperature is the material used to form any tooling that may contact the UHMWPE blend and substrate during irradiation. For example, a holder used to retain the UHMWPE blend and substrate in a desired position during irradiation may rapidly increase in temperature at a faster rate than the UHMWPE blend. In order to substantially eliminate this concern, the tooling should have a heat capacity substantially equal to or greater than the heat capacity of the UHMWPE blend. In one exemplary embodiment, the UHMWPE blend has a heat capacity substantially between 1.9 J/g° C. and 10 J/g° C. Thus, polyether ether ketone, for example, having a heat capacity of approximately 2.8 J/g° C., may be used to form the tooling. Alternative materials that may be used to form the tooling also include carbon fiber and other composites.

After the desired preheat temperature of the UHMWPE blend is achieved, the UHMWPE blend is subsequently irradiated at Steps 26, 28 to induce crosslinking of the UHMWPE. Thus, as used herein, "crosslinking irradiation" refers to exposing the UHMWPE blend to ionizing irradiation to form free radicals which may later combine to form crosslinks. The irradiation may be performed in air at atmospheric pressure, in a vacuum chamber at a pressure substantially less then atmospheric pressure, or in an inert environment, i.e., in an argon environment, for example. The irradiation is, in one exemplary embodiment, electron beam irradiation. In another exemplary embodiment, the irradiation is gamma irradiation. In yet another exemplary embodiment, steps 26, 28 do not require irradiation, but instead utilize silane crosslinking. In one exemplary embodiment, crosslinking is induced by exposing the UHMWPE blend to a total radiation dose between about 25 kGy and 1,000 kGy. In another exemplary embodiment, crosslinking is induced by exposing the UHMWPE blend to a total radiation dose between about 50 kGy and 250 kGy in air. These doses are higher than doses commonly used to crosslink UHMWPE due to the presence of tocopherol in the UHMWPE blend. Specifically, the tocopherol reacts with some of the polyethylene chains that became free radicals during irradiation. As a result, a higher irradiation dose must be administered to the UHMWPE blend to achieve the same level of crosslinking that would occur at a lower dose in standard UHMWPE, i.e., UHMWPE absent an antioxidant.

However, the higher irradiation dose needed to crosslink the UHMWPE blend to the same level as UHMWPE absent an antioxidant may cause a greater temperature increase in the UHMWPE blend. Thus, if the entire irradiation dose is administered to the UHMWPE blend at once, the UHMWPE blend may be heated above the melting point of the UHMWPE blend, approximately 140° C., and result in melt annealing of the UHMWPE blend. Therefore, prior to irradiating the UHMWPE blend, a determination is made at Steps 22, 24 comparing the total crosslinking irradiation dose to be administered to the UHMWPE blend to the maximum individual dose of radiation that can be administered to the UHMWPE blend without raising the temperature of the UHMWPE blend near to and/or above its melting point.

Thus, if the total crosslinking irradiation dose determined in Steps 22, 24 is less then the maximum individual crosslinking dose that can be administered without raising the temperature of the UHMWPE near to and/or above the melting point, the UHMWPE is irradiated and the total crosslinking irradiation dose identified at Steps 22, 24 is administered in air. In one exemplary embodiment, the maximum individual crosslinking dose is between about 50 kGy and 1000 kGy. In one exemplary embodiment, the maximum individual crosslinking dose is 150 kGy for the UHMWPE blend alone (Step 24) and is 100 kGy for the UHMWPE blend and substrate combination (Step 22). However, the maximum individual crosslinking dose may be any dose that does not cause the UHMWPE blend to increase in temperature above the melting point of the UHMWPE blend. Additionally, the maximum individual crosslinking dose may be dependent on the type of irradiation used. Thus, the maximum individual crosslinking dose for electron beam irradiation may be different than the maximum individual crosslinking dose for gamma irradiation. In one exemplary embodiment of the UHMWPE blend and substrate, a heat sink may be attached to the substrate to dissipate heat therefrom and allow for the use of a higher individual irradiation dose, i.e., allow for a higher dose to be administered in a single pass. Further, in addition to the type of irradiation used, the dose rate, temperature at which the dose is administered, the amount of time between doses, and the level of tocopherol in the UHMWPE blend, may also affect the maximum individual crosslinking dose.

If, at step 24, the total crosslinking dose for the UHMWPE blend is determined to exceed the maximum individual dose of approximately 150 kGy, multiple irradiation passes are required. Similarly, if, at Step 22, the total crosslinking dose for the UHMWPE blend and substrate exceeds the maximum individual dose of approximately 100 kGy, multiple irradiation passes are required. The lower maximum individual dose for the UHMWPE blend and substrate results from the greater potential temperature increase of the substrate during irradiation. This potential temperature increase may be sufficient to melt or otherwise significantly alter the UHMWPE blend along the UHMWPE blend/substrate interface. For example, as a result of the different coefficients of thermal expansion between the UHMWPE blend and the substrate, cracking may occur in the UHMWPE blend if irradiated at an individual dose in excess of the maximum individual dose.

For electron beam irradiation, the preheat temperature and dose level per pass are interdependent variables that are controlled by the specific heat of the materials being irradiated. The substrate material may heat to a significantly higher level than the polymer at the same irradiation dose level if the specific heat of the substrate is substantially lower than the specific heat of the polymer. The final temperature of the materials achieved during the irradiation can be controlled by a judicious choice of dose level per pass and preheat temperature, so that temperatures are high enough to promote crosslinking in the presence of tocopherol, but low enough to prevent substantial melting of the UHMWPE blend. Further, while partial melting may, in some embodiments, be desired, the final temperature should be low enough to prevent substantial melting and yet be high enough that free radical levels are reduced below the levels that would be present if no heating during irradiation had occurred. The propensity for cracking is most likely due to a combination of effects related to the weakness of the UHMWPE blend and expansion differences between the UHMWPE blend and substrate, whereas complete melting of the UHMWPE blend in the region near the substrate is due to overheating of the substrate.

If it is determined in Step 24 that multiple irradiation passes are required, as set forth above, then the first dose of irradiation administered in Step 28 should be less than 150 kGy. In one exemplary embodiment, the total irradiation dose determined in Step 24 is divided into equal, individual irradiation doses, each less than 150 kGy. For example, if the total irradiation dose determined in Step 24 is 200 kGy, individual doses of 100 kGy each may be administered. In another exemplary embodiment, at least two of the individual irradiation doses are unequal and all of the individual irradiation doses do not exceeded 150 kGy, e.g., a total crosslinking dose of 200 kGy is dividing into a first individual dose of 150 kGy and a second individual dose of 50 kGy.

Similarly, if it is determined in Step 22 that multiple irradiation passes are required, then the first dose of irradiation administered in Step 26 should be less than 100 kGy. In one exemplary embodiment, the total irradiation dose determined in Step 22 is divided into equal, individual irradiation doses, each less than 100 kGy. For example if the total irradiation dose determined in Step 22 is 150 kGy, individual doses of 75 kGy each may be administered. In another exemplary embodiment, at least two of the individual irradiation doses are unequal and all of the individual irradiation doses do not exceed 100 kGy, e.g., a total crosslinking dose of 150 kGy is divided into a first individual dose of 100 kGy and a second individual dose of 50 kGy.

Further, in the UHMWPE blend/substrate embodiment, by irradiating the UHMWPE blend first, i.e., directing the electron beam to contact the UHMWPE blend prior to contacting the substrate, the resulting UHMWPE blend has characteristics similar to an irradiated UHMWPE blend without the substrate and is generally suitable for normal applications. In contrast, by irradiating the substrate first, i.e., directing the electron beam to contact the substrate prior to contacting the UHMWPE blend, the resulting UHMWPE blend has characteristics that are substantially different than an irradiated UHMWPE blend without the substrate. Additionally, the differences, such as decreased crystallinity, are more pronounced near the UHMWPE blend/substrate interface and decrease as the UHMWPE blend moves away from the substrate.

In the event multiple irradiation passes are required as described in detail above, the temperature of the UHMWPE blend or UHMWPE blend and substrate may be equilibrated to the preheat temperature in Steps 30, 32, between the administration of the individual doses. Specifically, as a result of the first individual irradiation dose increasing the temperature of the UHMWPE blend, immediately administering another individual irradiation dose may significantly alter the material properties of the UHMWPE blend, melt the UHMWPE, or cause other detrimental effects. In one exemplary embodiment, after the first individual irradiation dose is administered, the UHMWPE blend or UHMWPE blend and substrate are removed and placed in an oven. The oven is set to maintain the temperature at the preheat temperature, i.e., the temperature used in Steps 18, 20 as described in detail above, and the UHMWPE blend or UHMWPE blend and substrate are placed within the oven to slowly cool until reaching the preheat temperature. Once the preheat temperature is reached, the UHMWPE blend or UHMWPE blend and substrate are removed and the next individual irradiation dose administered. In the event further individual irradiation doses are required, the temperature equilibration process is repeated.

In another exemplary embodiment, selective shielding is used to protect certain areas of the UHMWPE blend from exposure to the irradiation and substantially prevent or lessen the resulting temperature increase of the UHMWPE blend. Additionally, selective shielding may be used to help ensure that an even dose of irradiation is received by the UHMWPE blend. In one embodiment, a shield, such as a metallic shield, is placed in the path of the irradiation to attenuate the radiation dose received in the shielded area, while allowing the full effect of the irradiation dose in areas where higher temperatures can be tolerated. In one embodiment, the use of selective shielding allows for the total crosslinking irradiation dose to be administered in a single pass, reducing the need to administer the total crosslinking irradiation dose over multiple passes.

Additionally, selective shielding of the irradiation may be used to prevent the metallic substrate from excessive heating due to the differences in specific heats between the substrate and UHMWPE blend. The shielding could, in one exemplary embodiment, be designed so that the UHMWPE blend receives a substantially full irradiation dose, while lessening the irradiation penetration so that a reduced dose is received at the substrate. As a result, the temperature increase of the substrate due to irradiation absorption is decreased. This allows for the use of higher dose levels per pass, eliminating the need for multiple passes to achieve higher dose levels and thus higher levels of crosslinking. In some embodiments, single pass irradiation is advantageous since it is a more efficient manufacturing process, and the resulting mechanical properties of the crosslinked material may also be desirable. Specific aspects and methods of irradiation shielding are disclosed in U.S. Pat. No. 6,365,089, entitled METHOD FOR CROSSLINKING UHMWPE IN AN ORTHOPEDIC IMPLANT, issued on Apr. 2, 2002, the entire disclosure of which is expressly incorporated by reference herein.

In another exemplary embodiment, tocopherol is not added at Step 10, as discussed in detail above. Instead, tocopherol is diffused into the UHMWPE by placing the UHMWPE in a tocopherol bath after the UHMWPE has been irradiated in accordance with standard crosslinking irradiation techniques. However, as a result of administering the crosslinking irradiation prior to the addition of tocopherol, the present embodiment does not allow for the administration of a higher crosslinking irradiation dose, as discussed above. Additionally, the mechanical properties achieved by adding tocopherol prior to administering crosslinking irradiation appear to be superior to diffusing tocopherol into the UHMWPE after the crosslinking irradiation has been administered.

Figure 2:
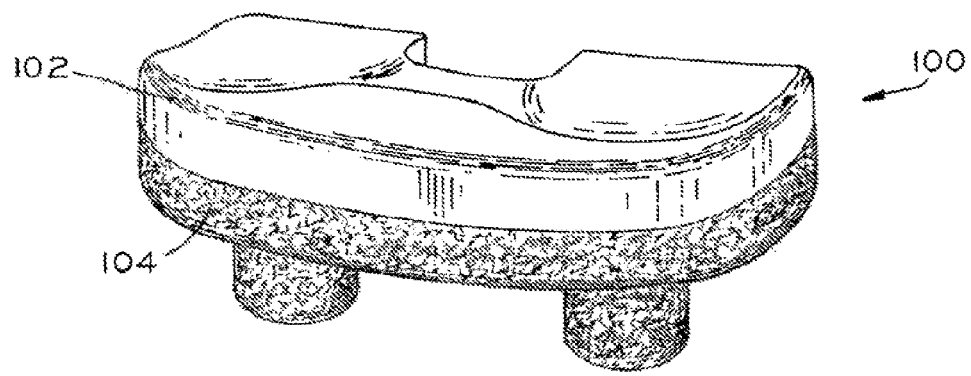
FIG. 2 is a perspective view of an exemplary medical implant formed form a UHMWPE blend and a substrate.
Figure 3:
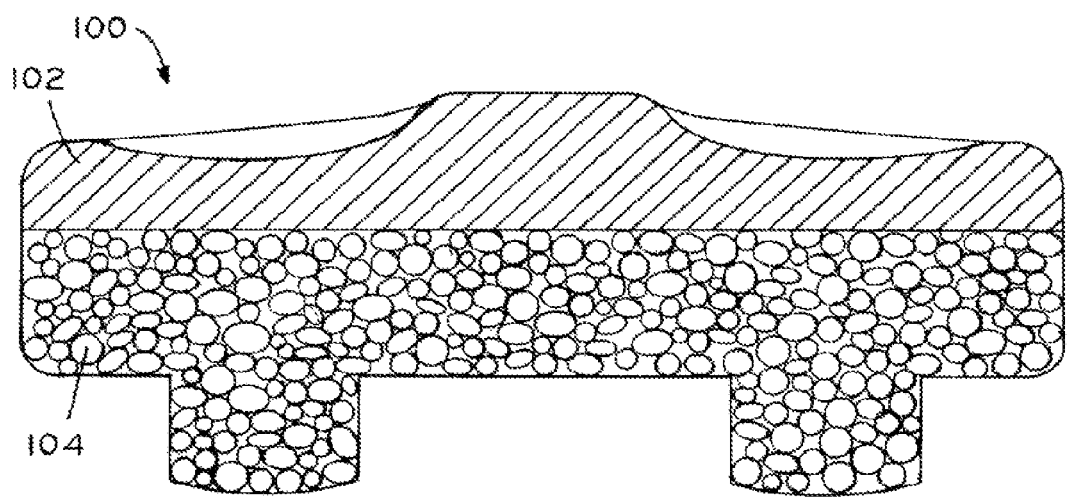
FIG. 3 is a cross-sectional view of the medical implant shown in FIG. 2.

Once the total crosslinking irradiation dose has been administered to the UHMWPE blend, the UHMWPE blend may be machined in Step 34 into a medical product, such as an orthopedic implant, according to customary techniques, such as milling, boring, drilling, cutting, and CNC (Computer Numerical Control) machining. For example, the UHMWPE blend may be machined into a hip, knee, ankle, shoulder, elbow, finger, dental, or spinal implant. Additionally, the UHMWPE blend may be assembled to other components for form a medical device. However, if the UHMWPE blend is processed at Step 12 in FIG. 1 by net shape molding, which is identified above as a potential processing method, the need to machine the UHMWPE blend at Step 34 is substantially eliminated. Specifically, if the UHMWPE blend is processed by net shape molding, the UHMWPE blend is formed to the final shape, i.e., the shape of the desired medical product, at Step 12, which may then be assembled to other components to form the final medical device. Referring to FIG. 2, an exemplary medical implant 100 is shown including UHMWPE blend 102 and substrate 104. As shown in FIG. 2, UHMWPE blend 102 is interdigitated with substrate 104 in a similar manner as described in U.S. patent application Ser. No. 11/055,322, entitled "MODULAR POROUS IMPLANT", filed Feb. 10, 2002, and U.S. Pat. No. 6,087,553, entitled "IMPLANTABLE METALLIC OPEN-CELLED LATTICE/POLYETHYLENE COMPOSITE MATERIAL AND DEVICES", issued on Jul. 11, 2000, the entire disclosures of which are expressly incorporated by reference herein.

The medical product may be packaged at Step 36 and sterilized at Step 38. In one exemplary embodiment, the medical product is sterilized using gas plasma. In another exemplary embodiment, the medical product is sterilized using ethylene oxide. In yet another exemplary embodiment, the medical product is sterilized using dry heat sterilization. Additionally, testing has indicated that surface sterilization techniques, such as gas plasma, dry heat, gamma radiation, ionizing radiation, autoclaving, supercritical fluid technique, and ethylene oxide, provide sufficient sterilization of the medical product, even if the UHMWPE blend is secured to a substrate. Specifically, the surface sterilization techniques have proven to sufficiently sterilize the UHMWPE blend/substrate interface. In another exemplary embodiment, gamma irradiation may be used to sterilize the medical product. However, in this embodiment, it is believed that a higher tocopherol concentration would be necessary in order for enough tocopherol to be available to quench free radicals after the sterilization irradiation was performed.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

EXAMPLES

The following non-limiting Examples illustrate various features and characteristics of the present invention, which is not to be construed as limited thereto. The following abbreviations are used throughout the Examples unless otherwise indicated.

TABLE 1

Abbreviations

| Abbreviation | Full Word |
|---|---|
| kGy | kilo Gray |
| min | minute |
| MeV | mega electron volt |
| m | meter |
| ° | degrees |
| C | Celsius |
| FTIR | Fourier Transform Infrared Spectroscopy |
| wt. % | weight percent |
| MPa | mega pascal |
| UTS | ultimate tensile strength |
| UHMWPE | ultrahigh molecular weight polyethylene |
| YS | yield strength |
| HXPE | highly crosslinked polyethylene |
| OI | Oxidation Index |
| T | Temperature |
| DSC | Differential Scanning Calorimetry |
| ml | milliliter |
| nm | nanometer |
| TVI | trans-vinylene index |
| VEI | d/l-α-tocopherol index |
| Mc | million cycles molecular weight between crosslinks |
| AVE | aged vitamin E percent |
| AVEI | aged vitamin E index |
| AV-OI | aged oxidation index |
| mg | milligram |
| cm | centimeter |
| IR | infrared |
| VE % | weight percent tocopherol |
| Vol | volume |
| wt. | weight |
| VE | tocopherol |
| g | gram |
| DMA | Dynamic Mechanical Analysis |
| kJ | kilojoule |
| Izod | Izod Impact Strength |
| Conc. | Concentration |
| dm | decimeter |

Throughout the various Examples, irradiated UHMWPE blends are used, which have been irradiated according to one of three different irradiation methods. As set forth above, differences in the irradiation conditions and techniques may affect the resulting material properties of the UHMWPE blend. Therefore, in order to properly analyze and compare the results set forth in the Examples and corresponding Tables, each of the irradiated UHMWPE blends used in the Examples are identified as having been irradiated according to the one of the methods set forth below in Table 2. Additionally, the electron beam source is calibrated by performing dosimetry at low irradiation doses and then parametrically determining the activation of the electron beam source needed to achieve higher doses. As a result, at higher irradiation doses, differences may exist between the actual dose and the parametrically determined dose, which may cause differences in the material properties of the irradiated UHMWPE blends.

TABLE 2

Irradiation Methods

| | Method A | Method B | Method C |
|---|---|---|---|
| Dose Rate (kGy-m/min) | 30-75 | 16-25 | 75-240 |
| Dose Level (kGy) | 160-190 | 133-217 | 90-200 |
| Electron Beam Energy (MeV) | 10 | 12 | 10 |
| Method of Dosimetry | Water Calorimeter | Aluminum Calorimeter | Radiochromic Film |

Example 1

Feasibility Study of α-Tocopherol Acetate

The feasibility of blending α-tocopherol acetate with UHMWPE was investigated. α-tocopherol acetate was obtained from DSM Nutritional Products, Ltd. of Geleen, Netherlands and medical grade UHMWPE powder GUR 1050 was obtained from Ticona, having North American headquarters located in Florence, Ky. Isopropanol was then added to the α-tocopherol acetate as a diluent and the α-tocopherol acetate was solvent blended with the UHMWPE powder. The blending continued until two different UHMWPE/α-tocopherol acetate blends were obtained, one UHMWPE blend having 0.05 wt. % α-tocopherol acetate and the other UHMWPE blend having 0.5 wt. % α-tocopherol acetate. Each of the UHMWPE blends were then compression molded to form four one-inch-thick pucks. Two pucks of each UHMWPE blend, i.e., two pucks of the UHMWPE blend having 0.05 wt. % α-tocopherol acetate and two pucks of the UHMWPE blend having 0.5 wt. % α-tocopherol acetate, were preheated to 120° C. in a Grieve convection oven, available from The Grieve Corporation of Round Lake, Ill. The pucks were held at 120° C. for 8 hours. After the expiration of 8 hours, the pucks were irradiated at 10 MeV, 50 kGy-m/min dose rate at 65 kGy and 100 kGy dose at Iotron Industries Canada Inc. located in Port Coquitlam, BC, Canada.

The remaining two pucks of each UHMWPE blend, i.e., two pucks of the UHMWPE blend having 0.05 wt. % α-tocopherol acetate and two pucks of the UHMWPE blend having 0.5 wt. % α-tocopherol acetate, were heated to 40° C. overnight. The next morning, the remaining two pucks of each UHMWPE blend were irradiated at 10 MeV, 50 kGy-m/min dose rate at 100 kGy dose at Iotron Industries Canada Inc. located in Port Coquitlam, BC, Canada.

Figure 5:
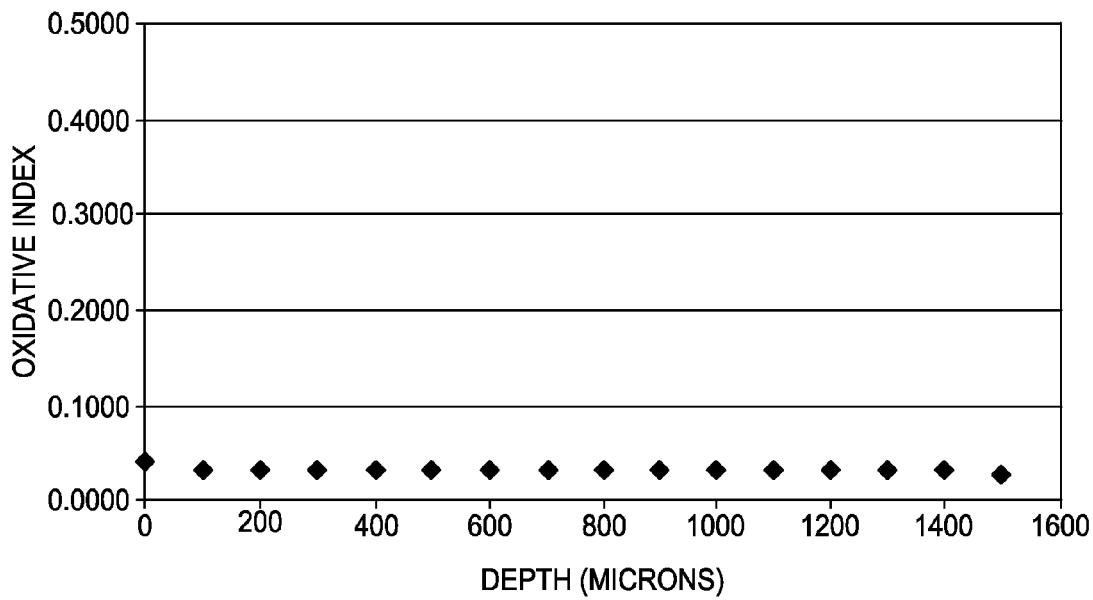
FIG. 5 depicts the oxidative index of an UHMWPE blend with 0.50 weight percent α-tocopherol acetate, in accordance with various embodiments.

After irradiation, all of the pucks were cut in half and a film was cut from the center of each puck. The films were then subjected to FTIR analysis using a Bruker Optics FTIR Spectrometer, available from Bruker Optics of Billerica, Mass. Both halves of each puck were then machined into flat sheets approximately ⅛ inch thick. One half of the flat sheets were immediately subjected to FTIR. The other half of the flat sheets were then subjected to accelerated aging in accordance with the American Society for Testing and Materials (ASTM) Standard F-2003, Standard Practice for Accelerated Aging of Ultra-High Molecular Weight Polyethylene after Gamma Irradiation in Air. Tensile specimens formed from the flat sheets were subjected to accelerated aging and were then subjected to FTIR analysis. The OI and wt. % of α-tocopherol acetate were determined from the FTIR results, set forth below in TABLE 3 and FIG. 5. However, there were interference peaks in the FTIR results that prevented measurement of OI for the 0.5 wt. %, 65 kGy, unaged sample.

TABLE 3

FTIR Results

| wt. % tocopherol | Dose, kGy | Condition | OI | wt. % tocopherol, meas. |
|---|---|---|---|---|
| 0.50 | 100 | Un-aged | <0/<0 | 0.17/0.15 |
|  |  | Aged | 0.0323 | 0.15 |
| 0.50 | 65 | Un-aged | *interference* | 0.14/0.15 |
|  |  | Aged | 0.0083 | 0.14 |
| 0.05 | 100 | Un-aged | 0.0300/0.0948 | 0.01/0.00 |
|  |  | Aged | 0.0647 | <0 |
| 0.05 | 65 | Un-aged | 0.0376/0.0940 | 0.02/0.00 |
|  |  | Aged | 0.0647 | <0 |

The FTIR results revealed that the OI of the UHMWPE blend having 0.05 wt. % α-tocopherol acetate was generally higher than the OI of the UHMWPE blend having 0.50 wt. % α-tocopherol acetate. This is believed to be because these samples still contained α-tocopherol acetate after irradiation. As a result, the α-tocopherol acetate was still available in these samples to react with free radicals and reduce the oxidative degradation of the UHMWPE blend. Additionally, the FTIR results showed that virtually no α-tocopherol acetate was left after irradiation of the UHMWPE blend having 0.05 wt. % α-tocopherol acetate and that about one-third of the α-tocopherol acetate was left after irradiation of the UHMWPE blend having 0.5 wt. % α-tocopherol acetate. Further, as shown in TABLE 5 below, tensile properties were similar for both the UHMWPE blends that were subjected to accelerated aging and the UHMWPE blends that were not subjected to accelerated aging. Finally, the FTIR results suggested that the UHMWPE blends containing α-tocopherol acetate have similar stabilization properties, i.e., a similar ability to prevent oxidative degeneration, as UHMWPE blends containing similar concentration of d,l-α-tocopherol.

TABLE 4

Mechanical Properties

| wt. % α-tocopherol acetate | Dose, kGy (Temperature) | Condition | Elongation, % | Yield, MPa | UTS, MPa |
|---|---|---|---|---|---|
| 0.50 | 100 (40° C.) | Un-aged | 356.7 | 23.1 | 61.7 |
|  |  | Aged | 360.1 | 25.3 | 65.3 |
| 0.50 | 65 (120° C.) | Un-aged | 384.6 | 21.8 | 61.4 |
|  |  | Aged | 378.4 | 24.2 | 65.1 |
| 0.05 | 100 (40° C.) | Un-aged | 342.9 | 21.5 | 56.7 |
|  |  | Aged | 288.6 | 25.2 | 61.0 |
| 0.05 | 65 (120° C.) | Un-aged | 352.4 | 21.4 | 57.4 |
|  |  | Aged | 287.7 | 25.2 | 59.6 |

Example 2

Chemical Properties of UHMWPE Blended with Tocopherol

The chemical properties of d/1-α-tocopherol mechanically blended with a UHMWPE powder which was slab molded into bars and electron beam irradiated were investigated. To perform this investigation, Design Expert 6.0.10 software, obtained from Stat-Ease, Inc. Minneapolis, Minn., was utilized to setup a modified fractional factorial Design of Experiment (DOE). The DOE evaluated five different variables: UHMWPE resin type, wt. % of d/1-α-tocopherol, preheat temperature, dose rate, and irradiation dose.

GUR 1050 and GUR 1020 medical grade UHMWPE powders were obtained from Ticona, having North American headquarters in Florence, Ky. d/1-α-tocopherol was obtained from DSM Nutritional Products, Ltd. of Geleen, Netherlands. The GUR 1050 and GUR 1020 were separately mechanically blended with the d/1-α-tocopherol by low intensity blending using a Diosna P100 Granulator, available from Diosna GmbH of Osnabrück, Germany, a subsidiary of Multimixing S.A. Both the GUR 1050 and the GUR 1020 resins were mixed with the d/1-α-tocopherol in several batches to create UHMWPE blends of both resin types having 0.2 wt. %, 0.5 wt. %, and 1.0 wt. % d/1-α-tocopherol. Each batch of blended material was compression molded into a slab and cut into bars of various sizes. Each of the resulting bars was then preheated by heating to a preheat temperature in a Grieve convection oven, available from The Grieve Corporation of Round Lake, Ill. The preheat temperature was selected from 40° C., 100° C., 110° C. and 122.2° C., as set forth in TABLE 5 below.

After being preheated, the UHMWPE blend bars were electron beam irradiated according to Method C, set forth in TABLE 2 above, at a selected dose rate until a selected total irradiation dose was administered. The dose rate was selected from 75 kGy-m/min, 155 kGy-m/min, and 240 kGy-m/min and the total irradiation dose was selected from 90 kGy, 120 kGy, 150 kGy, and 200 kGy. The portion of each bar was then microtomed into 200 micron thick films. These films were then subjected to FTIR analysis on a Broker Optics FTIR spectrometer, available from Broker Optics of Billerica, Mass. The FTIR results were analyzed to determine the VEI, wt. % d/1-α-tocopherol, the OI, and the TVI. The VEI and wt. % d/1-α-tocopherol were determined by calculating the ratio of the area under the d/1-α-tocopherol peak at 1275-1245 $cm^{-1}$ on the resulting FTIR chart to the area under the polyethylene peak at 1392-1330 $cm^{-1}$ and at 1985-1850 $cm^{-1}$. The OI was determined by calculating the ratio of the area under the carbonyl peak on the FTIR chart at 1765-1680 $cm^{-1}$ to the area of the polyethylene peak at 1392-1330 $cm^{-1}$. The TVI was determined by calculating the ratio of the area on the FTIR chart under the vinyl peak at 980-947 $cm^{-1}$ to the area under the polyethylene peak at 1392-1330 $cm^{-1}$.

After the initial VEI, wt. % d/1-α-toeopherol and TVI were determined from the FTIR analysis of the thin films, each of the thin films were accelerated aged according to ASTM Standard F-2003, Standard Practice for Accelerated Aging of Ultra-High Molecular Weight Polyethylene after Gamma Irradiation in Air. The accelerated aged films were again subjected to FTIR analysis on a Bruker Optics FTIR spectrometer, available from Bruker Optics of Billerica, Mass. The resulting FTIR charts were analyzed to determine VEI, wt. % d/1-α-tocopherol, OI, and TVI according to the methods set forth above. Once subjected to FTIR analysis, the aged files were placed in boiling hexane and allowed to remain there for 24 hours to extract the d/1-α-tocopherol. After extraction of the d/1-α-tocopherol, the aged films were again subjected to FTIR analysis on the Bruker Optics FTIR spectrometer. The resulting FTIR chart was then analyzed to determine the OI in accordance with the method set forth above. The additional FTIR analysis was performed to eliminate the d/1-α-tocopherol peak from interfering with the oxidation peaks. An analysis of the results set forth in TABLE 5 below indicate that selecting a warmer preheat temperature may result in a lower or and may also result in some of the d/1-α-tocopherol remaining in the UHMWPE after irradiation.

TABLE 5

FTIR Results of Irradiated UHMWPE Blended with d/l-α-tocopherol

| Run | Pre-heat (°C.) | Dose (kGy) | VE level (°C.) | Dose Rate (kGy-m/min) | Resin Type (GUR) |
|---|---|---|---|---|---|
| 1 | 122 | 150 | 1 | 75 | 1020 |
| 2 | 40 | 200 | 0.2 | 155 | 1020 |
| 3 | 122 | 90 | 0.5 | 75 | 1020 |
| 4 | 122 | 200 | 0.2 | 155 | 1020 |
| 5 | 40 | 90 | 0.2 | 240 | 1050 |
| 6 | 122 | 90 | 0.2 | 75 | 1050 |
| 7 | 40 | 150 | 0.2 | 75 | 1050 |
| 8 | 122 | 150 | 0.2 | 75 | 1020 |
| 9 | 40 | 90 | 1 | 240 | 1050 |
| 10 | 40 | 200 | 0.5 | 155 | 1020 |
| 11 | 122 | 90 | 0.2 | 240 | 1020 |
| 12 | 40 | 90 | 1 | 75 | 1020 |
| 13 | 40 | 150 | 0.5 | 75 | 1020 |
| 14 | 122 | 150 | 0.2 | 240 | 1050 |
| 15 | 122 | 150 | 0.5 | 240 | 1020 |
| 16 | 40 | 150 | 0.2 | 240 | 1020 |
| 17 | 40 | 90 | 0.2 | 75 | 1020 |
| 18 | 122 | 200 | 0.5 | 155 | 1020 |
| 19 | 122 | 90 | 1 | 240 | 1020 |
| 20 | 40 | 150 | 1 | 240 | 1020 |
| 21 | 40 | 200 | 1 | 155 | 1020 |
| 22 | 122 | 200 | 1 | 155 | 1020 |
| 23 | 40 | 200 | 0.2 | 155 | 1050 |
| 24 | 122 | 200 | 0.2 | 155 | 1050 |
| 25 | 40 | 200 | 0.5 | 155 | 1050 |
| 26 | 122 | 200 | 0.5 | 155 | 1050 |
| 27 | 40 | 200 | 1 | 155 | 1050 |
| 28 | 122 | 200 | 1 | 155 | 1050 |
| 29 | 40 | 120 | 0.5 | 157.5 | 1050 |
| 30 | 122 | 120 | 0.5 | 157.5 | 1050 |
| 31 | 40 | 120 | 1 | 157.5 | 1050 |
| 32 | 122 | 120 | 1 | 157.5 | 1050 |
| 33 | 40 | 90 | 1 | 75 | 1050 |
| 34 | 122 | 90 | 0.5 | 75 | 1050 |
| 35 | 40 | 150 | 0.5 | 75 | 1050 |
| 36 | 122 | 150 | 1 | 75 | 1050 |
| 37 | 40 | 90 | 0.5 | 240 | 1050 |
| 38 | 122 | 90 | 1 | 240 | 1050 |
| 39 | 40 | 150 | 1 | 240 | 1050 |
| 40 | 122 | 150 | 0.5 | 240 | 1050 |

| Run | VE % 1370 nm IR peak | VE % 1900 nm IR peak | VE Index 1370 nm IR peak | VE Index 1900 nm IR peak | VE % (aged) 1370 nm IR peak | VE % (aged) 1900 nm IR peak | VE Index (aged) 1370 nm IR peak | VE Index (aged) 1900 nm IR peak | OI (Extraction-aged) FTIR | TVI FTIR | TVI (aged) FTIR |
|---|---|---|---|---|---|---|---|---|---|---|---|
| 1 | 0.803 | 0.682 | 0.046 | 0.171 | 0.493 | 0.425 | 0.029 | 0.108 | −0.010 | 0.061 | 0.062 |
| 2 | 0.040 | 0.048 | 0.004 | 0.015 | 0.022 | 0.033 | 0.003 | 0.011 | 0.078 | 0.073 | 0.072 |
| 3 | 0.359 | 0.321 | 0.021 | 0.082 | 0.248 | 0.226 | 0.015 | 0.059 | −0.008 | 0.046 | 0.052 |
| 4 | 0.045 | 0.054 | 0.004 | 0.016 | 0.037 | 0.048 | 0.004 | 0.015 | 0.025 | 0.081 | 0.082 |
| 5 | 0.047 | 0.055 | 0.004 | 0.016 | 0.063 | 0.068 | 0.005 | 0.020 | 0.039 | 0.039 | 0.040 |
| 6 | 0.061 | 0.071 | 0.005 | 0.020 | 0.073 | 0.080 | 0.006 | 0.023 | 0.000 | 0.054 | 0.048 |
| 7 | 0.011 | 0.025 | 0.003 | 0.009 | 0.017 | 0.029 | 0.003 | 0.010 | 0.086 | 0.068 | 0.064 |
| 8 | 0.031 | 0.042 | 0.004 | 0.013 | 0.033 | 0.042 | 0.004 | 0.013 | 0.035 | 0.076 | 0.074 |
| 9 | 0.194 | 0.165 | 0.012 | 0.044 | 0.272 | 0.231 | 0.017 | 0.060 | 0.011 | 0.048 | 0.040 |
| 10 | 0.731 | 0.626 | 0.042 | 0.157 | 0.545 | 0.468 | 0.032 | 0.118 | 0.005 | 0.076 | 0.077 |
| 11 | 0.075 | 0.078 | 0.006 | 0.022 | 0.081 | 0.084 | 0.006 | 0.024 | 0.007 | 0.055 | 0.054 |
| 12 | 0.882 | 0.738 | 0.050 | 0.185 | 0.417 | 0.359 | 0.025 | 0.091 | −0.001 | 0.034 | 0.035 |
| 13 | 0.286 | 0.222 | 0.017 | 0.058 | 0.274 | 0.211 | 0.017 | 0.055 | 0.082 | 0.075 | 0.074 |
| 14 | 0.058 | 0.072 | 0.005 | 0.021 | 0.056 | 0.070 | 0.005 | 0.020 | 0.001 | 0.072 | 0.072 |
| 15 | 0.162 | 0.151 | 0.011 | 0.040 | 0.279 | 0.244 | 0.017 | 0.063 | 0.025 | 0.081 | 0.084 |
| 16 | 0.051 | 0.053 | 0.005 | 0.016 | 0.050 | 0.052 | 0.005 | 0.016 | 0.075 | 0.063 | 0.062 |
| 17 | 0.078 | 0.076 | 0.006 | 0.022 | 0.044 | 0.048 | 0.004 | 0.015 | 0.098 | 0.045 | 0.045 |
| 18 | 0.721 | 0.634 | 0.041 | 0.159 | 0.524 | 0.458 | 0.030 | 0.116 | −0.004 | 0.083 | 0.085 |
| 19 | 0.769 | 0.688 | 0.044 | 0.173 | 0.430 | 0.392 | 0.025 | 0.100 | −0.010 | 0.041 | 0.047 |
| 20 | 0.781 | 0.597 | 0.044 | 0.150 | 0.531 | 0.409 | 0.031 | 0.104 | 0.087 | 0.080 | 0.078 |
| 21 | 0.769 | 0.591 | 0.044 | 0.149 | 0.560 | 0.429 | 0.032 | 0.109 | 0.061 | 0.081 | 0.087 |
| 22 | 0.765 | 0.607 | 0.044 | 0.153 | 0.575 | 0.457 | 0.033 | 0.116 | −0.007 | 0.092 | 0.091 |
| 23 | 0.028 | 0.034 | 0.003 | 0.011 | 0.016 | 0.025 | 0.003 | 0.009 | 0.120 | 0.078 | 0.079 |
| 24 | 0.051 | 0.053 | 0.005 | 0.016 | 0.041 | 0.045 | 0.004 | 0.014 | 0.032 | 0.084 | 0.085 |
| 25 | 0.288 | 0.249 | 0.018 | 0.064 | 0.281 | 0.241 | 0.017 | 0.062 | 0.009 | 0.075 | 0.073 |
| 26 | 0.320 | 0.282 | 0.019 | 0.073 | 0.309 | 0.268 | 0.019 | 0.069 | −0.002 | 0.085 | 0.083 |
| 27 | 0.284 | 0.222 | 0.017 | 0.058 | 0.281 | 0.220 | 0.017 | 0.057 | 0.024 | 0.080 | 0.079 |
| 28 | 0.308 | 0.241 | 0.019 | 0.062 | 0.295 | 0.229 | 0.018 | 0.059 | 0.042 | 0.094 | 0.096 |
| 29 | 0.613 | 0.550 | 0.035 | 0.139 | 0.489 | 0.429 | 0.028 | 0.109 | 0.040 | 0.053 | 0.058 |
| 30 | 0.753 | 0.700 | 0.043 | 0.176 | 0.445 | 0.421 | 0.026 | 0.107 | 0.000 | 0.063 | 0.064 |
| 31 | 0.283 | 0.240 | 0.017 | 0.062 | 0.279 | 0.236 | 0.017 | 0.061 | 0.063 | 0.061 | 0.061 |
| 32 | 0.306 | 0.288 | 0.019 | 0.074 | 0.259 | 0.244 | 0.016 | 0.063 | 0.004 | 0.065 | 0.066 |
| 33 | 0.779 | 0.706 | 0.044 | 0.177 | 0.429 | 0.397 | 0.025 | 0.101 | 0.036 | 0.040 | 0.041 |
| 34 | 0.328 | 0.314 | 0.020 | 0.080 | 0.209 | 0.205 | 0.013 | 0.053 | −0.005 | 0.049 | 0.051 |
| 35 | 0.143 | 0.125 | 0.010 | 0.034 | 0.247 | 0.211 | 0.015 | 0.055 | 0.067 | 0.072 | 0.068 |
| 36 | 0.803 | 0.758 | 0.046 | 0.190 | 0.442 | 0.423 | 0.026 | 0.107 | −0.012 | 0.055 | 0.058 |
| 37 | 0.332 | 0.291 | 0.020 | 0.075 | 0.262 | 0.234 | 0.016 | 0.061 | 0.029 | 0.041 | 0.048 |
| 38 | 0.741 | 0.731 | 0.042 | 0.183 | 0.390 | 0.391 | 0.023 | 0.099 | −0.004 | 0.038 | 0.042 |
| 39 | 0.790 | 0.658 | 0.045 | 0.165 | 0.524 | 0.440 | 0.030 | 0.111 | 0.043 | 0.073 | 0.076 |
| 40 | 0.327 | 0.301 | 0.020 | 0.077 | 0.282 | 0.262 | 0.017 | 0.068 | −0.004 | 0.068 | 0.068 |

Example 3

Free Radical Concentrations in UHMWPE Blended with d/1-α-Tocopherol

The impact of mechanically blending d/1-α-tocopherol with UHMWPE powder on free radical concentration of electron beam irradiated UHMWPE blend molded pucks was investigated. To perform this investigation, Design Expert 6.0.10 software, obtained from Stat-Ease, Inc. Minneapolis, Minn., was utilized to setup a modified central composite Design of Experiment (DOE). The DOE evaluated five factors: preheat temperature, dose rate, irradiation dose, d/1-α-tocopherol concentration, and predetermined hold time, i.e., the time elapsed between removal of the UHMWPE blend from the oven until the initiation of electron beam irradiation.

GUR 1050 medical grade UHMWPE powder was obtained from Ticona, having North American headquarters in Florence, Ky. d/1-α-tocopherol was obtained from DSM Nutritional Products, Ltd. of Geleen, Netherlands. The GUR 1050 UHMWPE power was mechanically blended with the d/1-α-tocopherol by high intensity blending using an Eirich Mixer, available from Eirich Machines, Inc. of Gurnee, Ill. The GUR 1050 resin was mixed with the d/1-α-tocopherol in several batches to create UHMWPE blends having between 0.14 and 0.24 wt. % d/1-α-tocopherol, as set forth below in TABLE 6.

Each of the UHMWPE blends were then compression molded into 2.5 inch diameter and 1 inch thick pucks. Each of the resulting pucks was then preheated by heating in a Grieve convection oven, available from The Grieve Corporation of Round Lake, Ill., to a preheat temperature. The preheat temperature was selected from between 85° C. and 115° C., as set forth in TABLE 6 below. The pucks were then removed from the convection oven and held for a predetermined period of time ranging between 7 minutes and 21 minutes, as set forth in TABLE 6 below. After the expiration of the predetermined hold time, the pucks were electron beam irradiated utilizing Method A of TABLE 2. The pucks were irradiated at a dose rate selected from between 30 kGy-m/min and 75 kGy-m/min until a total dose selected from between 160 kGy and 190 kGy was administered, as set forth in TABLE 6 below. Cylindrical cores approximately 1 inch long were machined from the pucks. The cylindrical cores were then analyzed using a Bruker EMX/EPR (electron paramagnetic resonance) spectrometer, which has a detection limit of $0.01 \times 10^{15}$ spins/gram and is available from Broker Optics of Billerica, Mass. The resulting analysis indicated that preheat temperature, percent d/1-α-tocopherol, and dose level were all significant factors in determining the resulting free radical concentration of the UHMWPE blend. Specifically, preheat temperature and d/1-α-tocopherol concentration had a negative correlation with the free radical concentration, while the total dose had a positive correlation with the free radical concentration.

TABLE 6

Free Radical Concentration of UHMWPE Blends After Various Processing

| Run | Block | Preheat (° C.) | Dose (kGy) | VE % | Dose Rate (kGy-m/min.) | Oven to Beam (minutes) | Free radicals (spins/gram × E10−16) |
|---|---|---|---|---|---|---|---|
| 1 | Block 1 | 85 | 190 | 0.11 | 30 | 7 | 2.87 |
| 2 | Block 1 | 115 | 190 | 0.11 | 30 | 7 | 1.09 |
| 3 | Block 1 | 115 | 190 | 0.11 | 30 | 21 | 2.01 |
| 4 | Block 1 | 85 | 190 | 0.11 | 30 | 21 | 3.7 |
| 5 | Block 1 | 115 | 160 | 0.11 | 30 | 7 | 1.09 |
| 6 | Block 1 | 85 | 160 | 0.11 | 30 | 7 | 2.55 |
| 7 | Block 1 | 115 | 160 | 0.11 | 30 | 21 | 1.5 |
| 8 | Block 1 | 85 | 160 | 0.11 | 30 | 21 | 2.77 |
| 9 | Block 1 | 85 | 160 | 0.22 | 75 | 7 | 2.37 |
| 10 | Block 1 | 115 | 160 | 0.22 | 75 | 7 | 0.826 |
| 11 | Block 1 | 85 | 160 | 0.22 | 75 | 21 | 2.46 |
| 12 | Block 1 | 115 | 160 | 0.22 | 75 | 21 | 1.38 |
| 13 | Block 1 | 115 | 190 | 0.22 | 75 | 7 | 0.786 |
| 14 | Block 1 | 85 | 190 | 0.22 | 75 | 7 | 3.22 |
| 15 | Block 1 | 115 | 190 | 0.22 | 75 | 21 | 1.28 |
| 16 | Block 1 | 85 | 190 | 0.22 | 75 | 21 | 2.94 |
| 17 | Block 1 | 100 | 175 | 0.165 | 52.5 | 14 | 2.46 |
| 18 | Block 1 | 100 | 175 | 0.165 | 52.5 | 14 | 2.66 |
| 19 | Block 1 | 100 | 175 | 0.165 | 52.5 | 14 | 2.98 |
| 20 | Block 1 | 100 | 175 | 0.165 | 52.5 | 14 | 3.03 |

Example 4

Mechanical Properties of UHMWPE Blended with d/1-α-Tocopherol

The mechanical properties of d/1-α-tocopherol mechanically blended with a UHMWPE powder which was slab molded into bars and electron beam irradiated were investigated. To perform this investigation, Design Expert 6.0.10 software, obtained from Stat-Ease, Inc. Minneapolis, Minn., was utilized to setup a modified fractional factorial Design of Experiment (DOE). The DOE evaluated five different variables: UHMWPE resin type, weight percent of d/1-α-tocopherol, preheat temperature, dose rate, and irradiation dose.

GUR 1050 and GUR 1020 medical grade UHMWPE powders were obtained from Ticona, having North American headquarters in Florence, Ky. d/1-α-tocopherol was obtained from DSM Nutritional Products, Ltd. of Geleen, Netherlands. The GUR 1050 and GUR 1020 were separately mechanically blended with the d/1-α-tocopherol by low intensity blending using a Diosna P100 Granulator, available from Diosna GmbH of Osnabrück, Germany, a subsidiary of Multimixing S.A. Both the GUR 1050 and the GUR 1020 resins were mixed with the d/1-α-tocopherol in several batches to create UHMWPE blends of both resin types having 0.2 wt. %, 0.5 wt. %, and 1.0 wt. % d/1-α-tocopherol. Each batch of blended material was compression molded into a slab and cut into bars. Each of the resulting bars was then preheated by heating the bars in a Grieve convection oven, available from The Grieve Corporation of Round Lake, Ill., to a preheat temperature. The preheat temperature was selected from 40° C., 100° C., 110° C. and 122.2° C., as set forth in TABLE 7 below.

After being preheated, the UHMWPE blend bars were electron beam irradiated according to Method C, set forth in TABLE 2 above, at a selected dose rate until a selected total irradiation dose was administered. The dose rate was selected from 75 kGy-m/min, 155 kGy-m/min, and 240 kGy-m/min and the total irradiation dose was selected from 90 kGy, 120 kGy, 150 kGy, 200 kGy, and 250 kGy. Type V tensile specimens, as defined by the American Society for Testing and Materials (ASTM) Standard D638, Standard Test Method for Tensile Properties of Plastics, were machined from each of the UHMWPE blend bars. The Type V tensile specimens were then subjected to ultimate tensile elongation, UTS, and YS testing in accordance with ASTM Standard D638. Izod specimens were also machined from each of the UHMWPE blend bars and tested for izod impact strength according to ASTM Standard D256, Standard Test Methods for Determining the Izod Pendulum Impact Resistance of Plastics. Dynamic mechanical analysis (DMA) specimens were also machined from each of the UHMWPE blend bars and tested using a Model DMA 2980 Dynamic Mechanical Analyzer from TA Instruments of New Castle, Del.

An analysis of the results indicates that the total irradiation dose had an influence on the izod impact strength, ultimate tensile elongation, and yield strength of the UHMWPE blends. Additionally, the preheat temperature had an influence on the ultimate tensile strength and yield strength. In contrast, the weight percent of d/1-α-tocopherol had an influence on ultimate tensile elongation and the dynamic mechanical analysis. Additional results from the testing are set forth below in TABLE 8.

TABLE 7

Mechanical Properties of UHMWPE Blended with d/1-α-tocopherol

| Std | Pre heat °C. | Dose kGy | VE Conc. | Dose Rate kGy-m/min | Resin | Izod kJ/m^2 | Elongation % | UTS MPa | YS MPa | DMA MPa |
|---|---|---|---|---|---|---|---|---|---|---|
| 1 | 40 | 90 | 0.2 | 75 | 1020 | 90.79 | Not Tested | | | 5.45 |
| 2 | 122.2 | 90 | 0.2 | 75 | 1050 | 74.8 | 348.8 | 50.38 | 21.72 | 6.12 |
| 3 | 40 | 150 | 0.2 | 75 | 1050 | 59.66 | 300.9 | 56.2 | 25.1 | 6.78 |
| 4 | 100 | 150 | 0.2 | 75 | 1020 | 66.05 | 314.8 | 52.42 | 25.24 | 5.76 |
| 5 | 40 | 90 | 1 | 75 | 1020 | 111.19 | Not Tested | | | 4.36 |
| 6 | 122.2 | 90 | 0.5 | 75 | 1020 | 91.55 | Not Tested | | | 5.1 |
| 7 | 40 | 150 | 0.5 | 75 | 1020 | 79.96 | 355.7 | 55.83 | 26.28 | 4.96 |
| 8 | 100 | 150 | 1 | 75 | 1020 | 81.25 | Not Tested | | | 4.78 |
| 9 | 40 | 90 | 0.2 | 240 | 1050 | 82.01 | 319.3 | 56.83 | 23.06 | 6.18 |
| 10 | 122.2 | 90 | 0.2 | 240 | 1020 | 84.5 | Not Tested | | | 5.43 |
| 11 | 40 | 150 | 0.2 | 240 | 1020 | 67.53 | 293.1 | 56.19 | 26.87 | 5.96 |
| 12 | 100 | 150 | 0.2 | 240 | 1050 | 67.75 | 307.2 | 52.95 | 25.21 | 6.31 |
| 13 | 40 | 90 | 1 | 240 | 1050 | 106.17 | 411.2 | 61.76 | 24.89 | 4.53 |
| 14 | 122.2 | 90 | 1 | 240 | 1020 | 94.66 | Not Tested | | | 4.83 |
| 15 | 40 | 150 | 1 | 240 | 1020 | 93.79 | Not Tested | | | 5.6 |
| 16 | 100 | 150 | 0.5 | 240 | 1020 | 73.08 | 342.2 | 51.54 | 23.39 | 5.22 |
| 17 | 40 | 120 | 0.5 | 157.5 | 1050 | 99.87 | 374.6 | 57.96 | 23.23 | 5.06 |
| 18 | 110 | 120 | 0.5 | 157.5 | 1050 | 90.67 | 363.6 | 50.97 | 22.15 | 5.42 |
| 19 | 40 | 120 | 1 | 157.5 | 1050 | 94.34 | 352.5 | 58.5 | 23.64 | 5.53 |
| 20 | 110 | 120 | 1 | 157.5 | 1050 | 85.01 | 344.9 | 48.98 | 21.95 | 5.72 |
| 21 | 40 | 90 | 1 | 75 | 1050 | 107.07 | 396.4 | 61.25 | 23.13 | 5.02 |
| 22 | 122.2 | 90 | 0.5 | 75 | 1050 | 93.44 | 375.8 | 51.47 | 21.92 | 5.7 |
| 23 | 40 | 150 | 0.5 | 75 | 1050 | 82.09 | 330.4 | 56.65 | 25.78 | 4.62 |
| 24 | 100 | 150 | 1 | 75 | 1050 | 88.28 | Not Tested | | | 5.4 |
| 25 | 40 | 90 | 0.5 | 240 | 1050 | 102.39 | 36.9 | 58.4 | 23.31 | 5.16 |
| 26 | 122.2 | 90 | 1 | 240 | 1050 | 96.6 | 381.9 | 50.3 | 21.29 | 5.44 |
| 27 | 40 | 150 | 1 | 240 | 1050 | 89.5 | Not Tested | | | 5.16 |
| 28 | 100 | 150 | 0.5 | 240 | 1050 | 78.51 | 332.9 | 50.18 | 22.08 | 5.6 |
| 29 | 40 | 200 | 0.2 | 155 | 1020 | 55.98 | 246.2 | 52.37 | 27.23 | 6.32 |
| 30 | 110 | 200 | 0.2 | 155 | 1020 | 52.98 | 268.4 | 48.28 | 24.82 | 6.05 |
| 31 | 40 | 200 | 0.5 | 155 | 1020 | 74.64 | 310.7 | 53.53 | 25.42 | 5.38 |
| 32 | 110 | 200 | 0.5 | 155 | 1020 | 65.47 | 309.1 | 49.13 | 24.21 | 5.31 |
| 33 | 40 | 200 | 1 | 155 | 1020 | 72.67 | 362.9 | 55.62 | 25.9 | 4.63 |
| 34 | 110 | 200 | 1 | 155 | 1020 | 66.62 | 349.7 | 50.45 | 24.24 | 4.93 |
| 35 | 40 | 200 | 0.2 | 155 | 1050 | 57.82 | 226.4 | 50.92 | 25.3 | 7.15 |
| 36 | 110 | 200 | 0.2 | 155 | 1050 | 59.04 | 259.4 | 46.4 | 23.7 | 6.57 |
| 37 | 40 | 200 | 0.5 | 155 | 1050 | 67.49 | 280.6 | 51.91 | 26.23 | 5.88 |
| 38 | 110 | 200 | 0.5 | 155 | 1050 | 64.6 | 304.8 | 51.23 | 25.14 | 5.7 |
| 39 | 40 | 200 | 1 | 155 | 1050 | 82.01 | 328.9 | 53.79 | 24.43 | 5.15 |
| 40 | 110 | 200 | 1 | 155 | 1050 | 69.42 | 329.7 | 49.54 | 23.12 | 5.27 |
| 41 | 100 | 150 | 0.2 | 240 | 1050 | Not Tested | 307.2 | 52.96 | 23.27 | Not Tested |
| 42 | 100 | 150 | 0.2 | 240 | 1020 | Not Tested | 288.6 | 49.28 | 23.35 | Not Tested |

Example 5

Wear Properties of UHMWPE Mixed with d,l-α-Tocopherol

The wear properties of UHMWPE mechanically blended with d,l-α-tocopherol and exposed to electron beam irradiation was investigated. To perform this investigation, Design Expert 6.0.10 software, obtained from Stat-Ease, Inc. Minneapolis, Minn., was utilized to setup a modified central composite Design of Experiment (DOE). The DOE evaluated five different variables: preheat temperature, dose rate, total dose administered, d,l-α-tocopherol concentration, and cooling period, i.e., the elapsed time from end of the preheat until initial exposure to irradiation.

GUR 1050 medical grade UHMWPE powder was obtained from Ticona, having North American headquarters in Florence, Ky. d/1-α-tocopherol was obtained from DSM Nutritional Products, Ltd of Geleen, Netherlands. The GUR 1050 was mechanically mixed with the d/1-α-tocopherol using a High Intensity Mixer, available from Eirich Machines of Gurnee, Ill. The GUR 1050 resin was mixed with the d/1-α-tocopherol in several batches to create UHMWPE blends having a selected wt. % of d/1-α-tocopherol. The wt. % of d/1-α-tocopherol was selected from 0.14 wt. %, 0.19 wt. %, and 0.24 wt. % d/1-α-tocopherol. Each of the blends were then consolidated and formed into 2.5 inch diameter and 1 inch thick pucks. Each of the resulting pucks was then preheated by heating the pucks in a Grieve convection oven, available from The Grieve Corporation of Round Lake, Ill., to a preheat temperature. The preheat temperature was selected from 85° C., 100° C., and 115° C., as set forth in TABLE 8 below.

After being preheated, the UHMWPE blend pucks were then removed from the convection oven for a cooling period. The cooling period was selected from 7 minutes, 14 minutes, and 21 minutes, as set forth in TABLE 8 below. The pucks were then electron beam irradiated according to Method A, set forth in TABLE 2 above, at a selected dose rate until a selected total irradiation dose was administered. The dose rate was selected from 30 kGy-m/min, 52.5 kGy-m/min, and 75 kGy-m/min and the total irradiation dose was selected from 160 kGy, 175 kGy, and 190 kGy.

Pin-on-disc (POD) specimens in the form cylinders having a 9 mm diameter and 13 mm thickness were then machined from the UHMWPE blend pucks. A bidirectional pin-on-disc wear tester was then used to measure the wear rate of UHMWPE pins articulating against polished cobalt-chrome discs lubricated by 100% bovine serum. These measurements were made in accordance with the teachings of Bragdon, C. R., et al., in *A new pin-on-disk wear testing method for simulating wear of polyethylene on cobalt-chrome alloy in total hip arthroplasty*, published in the Journal of Arthroplasty, Vol. 16, Issue 5, 2001, on pages 658-65, the entire disclosure of which is expressly incorporated by reference herein. The bidirectional motion for the pin-on-disc wear tester was generated by a computer controlled XY table, available from the Compumotor Division of Parker Hannifin of Cleveland, Ohio, which was programmed to move in a 10 mm by 5 mm rectangular pattern. Affixed atop the XY table was a basin containing six cobalt-chrome discs polished to an implant quality finish. The XY table and basin were mounted on a servo-hydraulic MTS machine, available from MTS of Eden Prairie, Minn. The MTS machine then loaded the UHMWPE blend pin specimens against the polished cobalt-chrome discs.

The MTS machine was programmed to produce a Paul-type curve in synchronization with the motion of the XY table. A Paul-type curve is explained in detail in *Forces Transmitted By Joints in the Human Body* by J. P. Paul and published by in the Proceedings Institution of Mechanical Engineers at Vol. 181, Part 37, pages 8-15, the entire disclosure of which is expressly incorporated by reference herein. The peak load of the Paul-type loading curve corresponded to a peak contact pressure of 6.5 MPa between each of the UHMWPE pin specimens and the cobalt-chrome discs. Tests were conducted at 2 Hz to a total of $1.128 \times 10^6$ cycles. Analysis of the results indicated that the wear properties are affected by both the concentration of d/1-α-tocopherol and the total irradiation dose. Specifically, the results indicated that increasing the d/1-α-tocopherol concentration increased the wear rate of the UHMWPE blends, while increasing the total irradiation dose decreased the wear rate of the UHMWPE blends. Additionally, the results indicated that both dose rate and the cooling period had substantially no impact on the wear rate of the UHMWPE.

TABLE 8

Wear Properties of UHMWPE Mixed with d/1-α-tocopherol

| Run | Block | Preheat (° C.) | Dose (kGy) | VE % | Dose Rate (kGy-m/min.) | Oven to Beam (minutes) | POD Wear (mg/Mc) |
| --- | --- | --- | --- | --- | --- | --- | --- |
| 1 | Block 1 | 85 | 190 | 0.11 | 30 | 7 | 0.96 |
| 2 | Block 1 | 115 | 190 | 0.11 | 30 | 7 | 1.14 |
| 3 | Block 1 | 115 | 190 | 0.11 | 30 | 21 | 0.76 |
| 4 | Block 1 | 85 | 190 | 0.11 | 30 | 21 | 0.81 |
| 5 | Block 1 | 115 | 160 | 0.11 | 30 | 7 | 1.86 |
| 6 | Block 1 | 85 | 160 | 0.11 | 30 | 7 | 1.37 |
| 7 | Block 1 | 115 | 160 | 0.11 | 30 | 21 | 1.53 |
| 8 | Block 1 | 85 | 160 | 0.11 | 30 | 21 | 1.57 |
| 9 | Block 1 | 85 | 160 | 0.22 | 75 | 7 | 2.94 |
| 10 | Block 1 | 115 | 160 | 0.22 | 75 | 7 | 2.15 |
| 11 | Block 1 | 85 | 160 | 0.22 | 75 | 21 | 2.41 |
| 12 | Block 1 | 115 | 160 | 0.22 | 75 | 21 | 1.96 |
| 13 | Block 1 | 115 | 190 | 0.22 | 75 | 7 | 2.57 |
| 14 | Block 1 | 85 | 190 | 0.22 | 75 | 7 | 1.87 |
| 15 | Block 1 | 115 | 190 | 0.22 | 75 | 21 | 1.87 |
| 16 | Block 1 | 85 | 190 | 0.22 | 75 | 21 | 2.24 |
| 17 | Block 1 | 100 | 175 | 0.165 | 52.5 | 14 | 0.89 |
| 18 | Block 1 | 100 | 175 | 0.165 | 52.5 | 14 | 1.18 |
| 19 | Block 1 | 100 | 175 | 0.165 | 52.5 | 14 | 1.24 |
| 20 | Block 1 | 100 | 175 | 0.165 | 52.5 | 14 | 1.27 |

Example 6

Temperature Variations at the UHMWPE Blend/Substrate Interface

GUR 1050 medical grade UHMWPE powder was obtained from Ticona, having North American headquarters in Florence, Ky. d/1-α-tocopherol was obtained from DSM Nutritional Products, Ltd of Geleen, Netherlands. The GUR 1050 was mechanically blended with the d/1-α-tocopherol using a High Intensity Mixer, available from Eirich Machines of Gurnee, Ill. The GUR 1050 resin was mixed with the d/1-α-tocopherol to create a UHMWPE blend having 0.2 wt. % d/1-α-tocopherol.

A portion of the UHMWPE blend was then compression molded into a block. Another portion of the UHMWPE blend was compression molded into a substrate to create a preform. The substrate was a 70 mm diameter porous metal substrate in the form of a near-net shape acetabular shell. The porous metal substrate was produced using Trabecular Metal™ technology generally available from Zimmer, Inc., of Warsaw, Ind., and described in detail above. This process was repeated to create five different preforms. The preforms were then individually heated to a preheat temperature in a Grieve convection oven, available from The Grieve Corporation of Round Lake, Ill. The preheat temperature was selected from 100° C., 120° C., and 125° C. Once heated to the selected preheat temperature, the preforms were irradiated using Method B, set forth in TABLE 2 above, until a total irradiation dose was received. The total irradiation dose was selected from 50 kGy, 75 kGy, and 150 kGy. Additionally, the UHMWPE block was heated to a preheat temperature of 100° C. and irradiated using Method B until a total irradiation dose of 150 kGy was received by the UHMWPE block.

The temperature of the preforms was measured at the UHMWPE blend/substrate interface, at a point in the UHMWPE blend adjacent to the UHMWPE blend/substrate interface, and at a point in the center of the UHMWPE blend. Each of the temperature measures were taken using a Type J thermocouple. Additionally, the temperature at the center of the UHMWPE blend block was also measured using a Type J thermocouple. Based on the results, the presence of a porous substrate resulted in higher temperature readings in the UHMWPE blend. This is likely a result of substrate reaching a higher maximum temperature than the UHMWPE during irradiation.

Example 7

Effect of Substrate Orientation on UHMWPE Blend

GUR 1050 medical grade UHMWPE powder was obtained from Ticona, having North American headquarters in Florence, Ky. d/1-α-tocopherol was obtained from DSM Nutritional Products, Ltd of Geleen, Netherlands. The GUR 1050 was mechanically blended with the d/1-α-tocopherol using a High Intensity Mixer, available from Eirich Machines of Gurnee, Ill. The GUR 1050 resin was mixed with the d/1-α-tocopherol to create a UHMWPE blend having 0.5 wt. % d/1-α-tocopherol.

A portion of the UHMWPE blend was compression molded into a substrate to create a preform. The substrate was a 70 mm diameter porous metal substrate in the form of a near-net shape acetabular shell. The porous metal substrate was produced using Trabecular Metal™ technology generally available from Zimmer, Inc., of Warsaw, Ind., and described in detail above. This process was repeated to create three different preforms. The preforms were then heated in a convection oven to a preheat temperature of 110° C. for a minimum of 12 hours. Two of the preforms were then irradiated using Method A, as set forth in TABLE 2 above, with the substrate of one of the preforms facing the irradiation source and the substrate of the other preform facing away from the irradiation source. With the preforms in these positions, they were exposed to a first, 100 kGy dose of irradiation. The preforms were then allowed to sit in ambient air for 20 minutes. After the expiration of 20 minutes, the preforms were exposed to a second, 100 kGy dose of irradiation, for a total irradiation dose of 200 kGy.

The remaining preform was irradiated using Method B, as set forth in TABLE 2 above, with the substrate of the preform facing the irradiation source. With the preform in this position, the preform was exposed to a first, 100 kGy dose of irradiation. The preform was then placed in a convection oven which maintained a constant temperature of 110° C. After the expiration of four hours, the preform was removed from the convection oven and exposed to a second, 100 kGy dose of irradiation, for a total irradiation dose of 200 kGy.

Each of the preforms was then cut through the center and the substrate removed. The UHMWPE blend was then microtomed and subjected to FTIR analysis using a Bruker FTIR Spectrometer, available from Bruker Optics of Billerica, Mass., to determine the TVI of the UHMWPE blend. This analysis was performed on the thickest part of the specimens. A sample of the UHMWPE blend was then subjected to DSC using a TA Instruments Q1000, available from TA Instruments of New Castle, Del., to determine the percent crystallinity of the UHMWPE blend. This analysis was repeated for samples of the UHMWPE blend taken from different locations.

Figure 4:
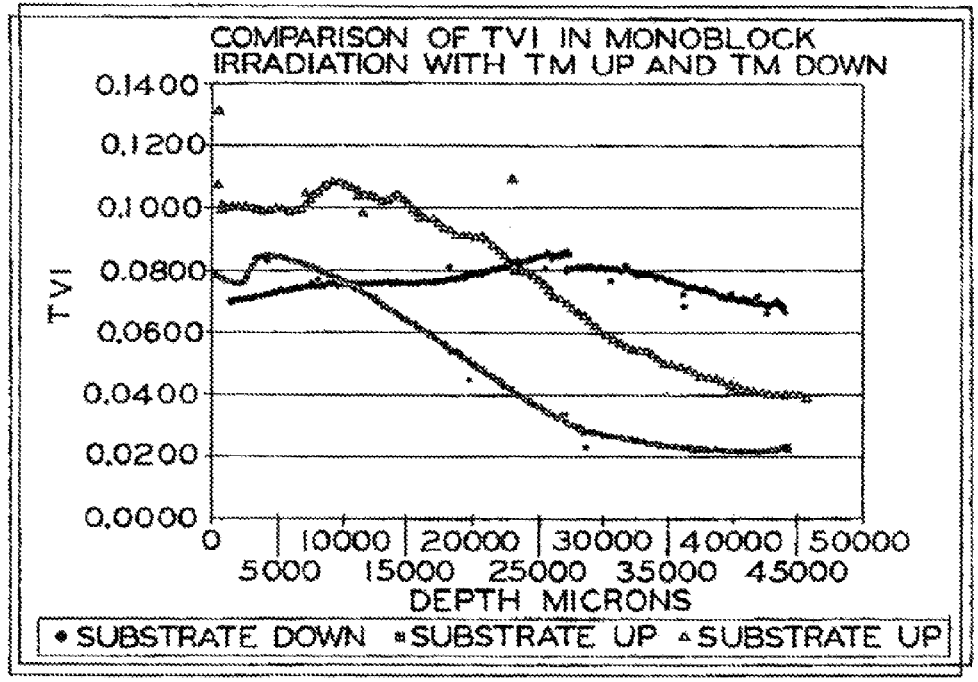
FIG. 4 depicts a graphical illustration of the TVI of an irradiated UHMWPE monoblock component.

In both of the monoblocks that were irradiated with the substrate facing the irradiation source, a band of discoloration, i.e., translucence, can be seen along the edge of the UHMWPE blend that interfaced with the substrate. As shown in FIG. 4, the FTIR analysis showed a substantial decline in the TVI of the UHMWPE blend at a point just past the interface between the UHMWPE blend and the substrate. Additionally, the percent crystallinity at a point in the center of the UHMWPE blend was approximately 59%. The percent crystallinity decreased as the UHMWPE blend approached the interface with the substrate, with the percent crystallinity reaching 48% in the translucent region near the UHMWPE blend/substrate interface, as shown in TABLE 9 below. In the preform that was irradiated with the substrate facing away from the irradiation source, the TVI of the UHMWPE blend was substantially more uniform throughout the UHMWPE blend and the percent crystallinity varied by only 2.2%. This may be a result of more uniform crosslinking occurring in the preform in which the substrate faced away from the irradiation source during irradiation.

TABLE 9

Percent Crystallinity of UHMWPE Blend

| Specimen | % Crysallinity at the center of the UHMWPE Blend | % Crystallinity at the UHMWPE Blend/Substrate Interface |
|---|---|---|
| Substrate Toward Irradiation Source | 59.29% | 48.67% |
| Substrate Toward Irradiation Source | 58.60% | 47.96% |
| Substrate Away from Irradiation Source | 58.88% | 57.66% |

Example 8

Effect of Irradiation Dose on UHMWPE Blend

Design Expert 6.0.10 software, obtained from Stat-Ease, Inc. Minneapolis, Minn., was utilized to setup a central composite response surface Design of Experiment (DOE). The DOE evaluated three different variables: d,l-α-tocopherol concentration, preheat temperature, total irradiation dose administered, and irradiation dose per pass.

GUR 1050 medical grade UHMWPE powder was obtained from Ticona, having North American headquarters in Florence, Ky. d/1-α-tocopherol was obtained from DSM Nutritional Products, Ltd of Geleen, Netherlands. The GUR 1050 was mechanically mixed with the d/1-α-tocopherol using a High Intensity Mixer, available from Eirich Machines of Gurnee, Ill. The GUR 1050 resin was mixed with the d/1-α-tocopherol in several batches to create UHMWPE blends having a selected wt. % of d/1-α-tocopherol. The wt. % of d/1-α-tocopherol was selected from 0.10 wt. %, 0.20 wt. %, 0.35 wt. %, 0.50 wt. %, and 0.60 wt. % d/1-α-tocopherol. Each of the blends was then compression molded into a substrate to create a preform. The substrate was a 70 mm outer diameter porous metal substrate in the form of a near-net shape acetabular shell. The porous metal substrate was produced using Trabecular Metal™ technology generally available from Zimmer, Inc., of Warsaw, Ind., and described in detail above.

The resulting preforms were then placed inside a piece of expandable braided polyethylene terephthalate sleeving and vacuum sealed inside an aluminum-metallized plastic film pouch, such a pouch formed from a polyethylene terephthalate resin, such as Mylar®, which has been coated with a metal, such as aluminum, to reduce gas diffusion rates through the film. Mylar is a registered trademark of DuPont Teijin Films U.S. Limited Partnership of Wilmington, Del. The preforms remained in this condition until they were removed in preparation for exposing the preforms to irradiation. Prior to irradiation, each of the resulting preforms was preheated by heating the preforms in a Grieve convection oven, available from The Grieve Corporation of Round Lake, Ill., to a preheat temperature, which was held for a minimum of 12 hours. The preheat temperature was selected from 60° C., 70° C., 85° C., 100° C., and 110° C., as set forth in TABLE 10 below.

The preforms were then exposed to a selected total irradiation dose according to Method B, as set forth above in TABLE 2. The total irradiation dose was selected from 133 kGy, 150 kGy, 175 kGy, 200 kGy, and 217 kGy. Additionally, the total irradiation dose was divided and administered to the preforms in either two equal passes or three equal passes, which are combined to achieve the total irradiation dose. Specifically, the preforms indicated to be "Block 1" in TABLE 10 below received the total irradiation dose in two equal passes, while the preforms indicated to be "Block 2" in TABLE 10 received the total irradiation dose in three equal passes.

After irradiation, each of the UHMWPE blends was separated from the substrate and three Pin-on-Disc (POD) specimens in the shape of cylinders having a 9 mm diameter and 13 mm thickness were then machined from the UHMWPE blend pucks. A bidirectional pin-on-disc wear tester was then used to measure the wear rate of UHMWPE pins articulating against polished cobalt-chrome discs lubricated by 100% bovine serum. These measurements were made in accordance with the teachings of Bragdon, C. R., et al., in *A new pin-on-disk wear testing method for simulating wear of polyethylene on cobalt-chrome alloy in total hip arthroplasty*, published in the Journal of Arthroplasty, Vol. 16, Issue 5, 2001, on pages 658-65, the entire disclosure of which is expressly incorporated by reference herein. The bidirectional motion for the pin-on-disc wear tester was generated by a computer controlled XY table, available from the Compumotor Division of Parker Hannifin of Cleveland, Ohio, which was programmed to move in a 10 mm by 5 mm rectangular pattern. Affixed atop the XY table was a basin containing six cobalt-chrome discs polished to an implant quality finish. The XY table and basin were mounted on a servo-hydraulic MTS machine, available from MTS of Eden Prairie, Minn. The MTS machine then loaded the UHMWPE blend pin specimens against the polished cobalt-chrome discs.

The MTS machine was programmed to produce a Paul-type curve [2] in synchronization with the motion of the XY table. A Paul-type curve is explained in detail in *Forces Transmitted By Joints in the Human Body* by J. P. Paul and published in the Proceedings Institution of Mechanical Engineers at Vol. 181, Part 37, pages 8-15, the entire disclosure of which is expressly incorporated by reference herein. The peak load of the Paul-type loading curve corresponded to a peak contact pressure of 6.5 MPa between each of the UHMWPE pin specimen and the cobalt-chrome discs. Tests were conducted at 2 Hz to a total of $1.128 \times 10^6$ cycles.

The remaining portions of the UHMWPE blends were cut in half to form microtome films that were subjected to FTIR analysis utilizing a Broker Optics FTIR Spectrometer, available from Broker Optics of Billerica, Mass. The films were then accelerated aged according to ASTM Standard F2003, Standard Guide for Accelerated Aging of Ultra-High Molecular Weight Polyethylene. The OI of the post-aged films was then measured.

Once the measurements were taken, the post-aged films were placed in boiling hexane for 24 hours to extract any d/1-α-tocopherol remaining in the films. The percentage of d/1-α-tocopherol extracted from the UHMWPE blend films was then determined. The remaining UHMWPE blend from the monoblock was then machined into 1/16" flats and Type V tensile specimens, as defined by ASTM Standard D638, Standard Test Method for Tensile Properties of Plastics, were machined from the flats.

An analysis of the results, set forth below in TABLE 10, indicated that wear increased with a lower total irradiation dose or with a higher concentration of d/1-α-tocopherol. Additionally, the d/1-α-tocopherol concentration had a significant impact on ultimate tensile elongation. The yield strength was affected the most by the preheat temperature, whereas UTS was affected the most by the total irradiation dose and d/1-α-tocopherol concentration. The OI was decreased with higher preheat temperatures and higher concentration of d/1-α-tocopherol. Although the percentage of d/1-α-tocopherol decreased after irradiation and aging, a significant amount of d/1-α-tocopherol still remained in the UHMWPE blend after irradiation and aging.

TABLE 10

Effect of Irradiation Dose on UHMWPE Blend

| Run | Block | Preheat (° C.) | Dose (kGy) | VE % | POD Wear (mg/Mc) |
|---|---|---|---|---|---|
| 1 | Block 1 | 100.00 | 200.00 | 0.20 | 1.01 |
| 2 | Block 1 | 100.00 | 150.00 | 0.50 | 3.84 |
| 3 | Block 1 | 100.00 | 150.00 | 0.20 | 1.59 |
| 4 | Block 1 | 100.00 | 200.00 | 0.50 | 1.78 |
| 5 | Block 2 | 59.77 | 175.00 | 0.35 | 1.97 |
| 6 | Block 1 | 70.00 | 150.00 | 0.20 | 1.76 |
| 7 | Block 1 | 70.00 | 200.00 | 0.20 | 0.80 |
| 8 | Block 1 | 70.00 | 150.00 | 0.50 | 3.91 |
| 9 | Block 1 | 70.00 | 200.00 | 0.50 | 2.38 |
| 10 | Block 2 | 110.23 | 175.00 | 0.35 | 2.05 |
| 11 | Block 2 | 85.00 | 132.96 | 0.35 | 3.32 |
| 12 | Block 2 | 85.00 | 175.00 | 0.60 | 2.34 |
| 13 | Block 2 | 85.00 | 175.00 | 0.10 | 0.58 |
| 14 | Block 2 | 85.00 | 175.00 | 0.35 | 2.28 |
| 15 | Block 2 | 85.00 | 217.04 | 0.35 | 1.06 |
| 16 | Block 1 | 85.00 | 175.00 | 0.35 | 1.94 |
| 17 | Block 2 | 85.00 | 175.00 | 0.35 | 2.30 |

| Run | Elongation % | YS (MPa) | UTS (MPa) | VE % (Aged) | OI (Aged) |
|---|---|---|---|---|---|
| 1 | 248.90 | 21.86 | 41.18 | 0.04 | 0.04 |
| 2 | 306.40 | 22.85 | 47.62 | 0.27 | 0.02 |
| 3 | 268.10 | 22.50 | 46.06 | 0.07 | 0.03 |
| 4 | 293.00 | 22.03 | 43.03 | 0.25 | 0.02 |
| 5 | 261.80 | 24.45 | 49.27 | 0.12 | 0.08 |
| 6 | 248.10 | 23.08 | 45.95 | 0.06 | 0.06 |
| 7 | 223.00 | 23.14 | 43.93 | 0.05 | 0.07 |
| 8 | 310.00 | 24.04 | 51.23 | 0.25 | 0.03 |
| 9 | 272.30 | 23.86 | 48.34 | 0.24 | 0.02 |
| 10 | 273.20 | 23.76 | 46.95 | 0.17 | 0.04 |
| 11 | 288.90 | 23.92 | 49.37 | 0.17 | 0.04 |
| 12 | 289.60 | 24.37 | 49.24 | 0.29 | 0.04 |
| 13 | 213.20 | 23.21 | 45.01 | −0.01 | 0.06 |
| 14 | 258.80 | 23.97 | 47.60 | 0.17 | 0.05 |
| 15 | 234.00 | 24.41 | 45.00 | 0.13 | 0.06 |
| 16 | 269.70 | 23.39 | 48.64 | 0.14 | 0.02 |
| 17 | 264.10 | 23.95 | 48.41 | 0.15 | 0.05 |

Example 9

Elution in Deionized Water

The amount of d/1-α-tocopherol eluted from UHMWPE blends formed into consolidated pucks was investigated over a period of 8 weeks. GUR 1050 medical grade UHMWPE powder was obtained from Ticona, having North American headquarters in Florence, Ky. d/1-α-tocopherol was obtained from DSM Nutritional Products, Ltd of Geleen, Netherlands. The GUR 1050 was mechanically mixed with the d/1-α-tocopherol using a High Intensity Mixer, available from Eirich Machines of Gurnee, Ill. The GUR 1050 resin was mixed with the d/1-α-tocopherol to create a UHMWPE blend having 0.25 wt. % of d/1-α-tocopherol. The UHMWPE blend was then compression molded into a series of 2.5 inch diameter and 1.5 inch thick pucks.

The pucks were preheated in a Grieve convection oven, available from The Grieve Corporation of Round Lake, Ill., to a preheat temperature. The preheat temperature was selected from 85° C. and 115° C. Once preheated, the pucks were then exposed to a selected total irradiation dose according to Method A, as set forth above in TABLE 2. The total irradiation dose was selected from 160 kGy and 190 kGy. One centimeter cubes were then machined from the pucks and placed in glass jars containing 100 ml of deionized water. The jars were then sealed using Teflon® seals and caps, available from E.I. DuPont Nemours and Company. Teflon® is a registered trademark of E. I. DuPont Nemours and Company of 1007 Market Street, Wilmington Del.

Each of the glass jars was then placed in a water bath that was thermostatically held at a test temperature. The test temperature was selected from 37° C. and 70° C. At two week intervals, aliquots of extract solution were taken from each jar and assayed using 297 nm wavelength ultraviolet light to determine the concentration of d/1-α-tocopherol. Absorption measurements were made using 10 mm quartz cuvettes and deionized water as the reference material. Once the assay was completed, the test aliquots were returned to the glass jars. This analysis was repeated for a total of 53 days. As the results set forth below in TABLE 11 indicate, no eluted d/1-α-tocopherol was detected in the UHMWPE blend cubes that were soaked in deionized water maintained at 37° C. Additionally, no definitive elution of d/1-α-tocopherol was detected in the UHMWPE blend cubes that were soaked in deionized water maintained at 70° C. For example, the results showed that the antioxidant leached from 2 grams of the crosslinked UHMWPE in 100 milliliters of 37 degree Celsius water after 53 days resulted in an extraction solution absorbance at 297 nanometers was no greater than 0.01 units from the reference water absorbance.

TABLE 11

Elution of d/1-α-tocopherol in Deionized Water

| Group # | Solvent | Temperature (C.) | Solvent Wt (g) - Vol (mL) | Sample Weight (g) | 53 Day Water Raw A @ 297 nm | 53 Day Water Net A @ 297 nm |
|---|---|---|---|---|---|---|
| A | Water | 37 | 100 | 1.91335 | −0.0017 | 0.000 |
| A | Water | 70 | 100 | 1.90159 | 0.0032 | 0.005 |
| B | Water | 37 | 100 | 1.91722 | −0.0012 | 0.000 |
| B | Water | 70 | 100 | 1.91635 | 0.0043 | 0.006 |
| C | Water | 37 | 100 | 1.90948 | −0.0014 | 0.000 |
| C | Water | 70 | 100 | 1.91114 | 0.0030 | 0.005 |
| D | Water | 37 | 100 | 1.90083 | −0.0016 | 0.000 |
| D | Water | 70 | 100 | 1.92051 | 0.0036 | 0.005 |
| | Water Blank A | | | | −0.0016 | |

Example 10

Color Measurement of UHMWPE Blend Samples

GUR 1050 medical grade UHMWPE powder was obtained from Ticona, having North American headquarters in Florence, Ky. d/1-α-tocopherol was obtained from DSM Nutritional Products, Ltd of Geleen, Netherlands. The GUR 1050 was mechanically blended with the d/1-α-tocopherol using a High Intensity Mixer, available from Eirich Machines of Gurnee, Ill. The GUR 1050 resin was mixed with the d/1-α-tocopherol to create a UHMWPE blend having less than 0.5 wt. % d/1-α-tocopherol and was compression molded. The compression molded UHMWPE blend was then sectioned and subjected to analysis with a spectrophotometer to determine the color of the UHMWPE blend. Additionally, consolidated UHMWPE powder absent tocopherol was also subjected to analysis with a spectrophotometer to determine the color of the consolidated UHMWPE absent tocopherol.

Specifically, a Color Checker 545 Portable Spectrophotometer hand held unit, available from X-Rite Incorporated of Grand Rapids, Mich., was used to test the material samples. This device uses a system illuminant D65 and has a degree observer, i.e., the placement of the device relative to the sample being tested, of 10 degrees. The device was calibrated using a calibration tile and the average results per reading were recorded for comparison with the test samples. Each of the samples were then subjected to analysis.

The results of each individual analysis were displayed on the device using the L*a*b* (CIELAB) color space definition system. This system describes all colors visible to the human eye by providing the lightness of the color, the position of the color between red/magenta and green, and the position of the color between yellow and blue. These results are displayed as L*, having a value from 0, which corresponds to black, to 100, which corresponds to white, a*, where a negative value indicates green and a positive value indicates red/magenta, and b*, where a negative value indicates blue and a positive value indicates yellow.

Based on the results of the testing, set forth in TABLE 12 below, the UHMWPE blend having tocopherol exhibited a yellowish color.

TABLE 12

Color Measurements of UHMWPE and UHMWPE w/ Tocopherol

| Material | L* | a* | b* |
|---|---|---|---|
| UHMWPE | 96.58 | −8.30 | 19.53 |
| UHMWPE | 96.72 | −8.34 | 19.49 |
| UHMWPE | 96.01 | −9.48 | 18.28 |
| UHMWPE Blend (0.5 VE %) | 96.15 | −7.93 | 20.48 |
| UHMWPE Blend (0.5 VE %) | 96.79 | −8.00 | 20.56 |
| UHMWPE Blend (0.5 VE %) | 95.40 | −9.10 | 19.23 |

Example 11

Swell Ratio, Crosslink Density, and Molecular Weight Between Crosslinks

GUR 1050 medical grade UHMWPE powder was obtained from Ticona, having North American headquarters in Florence, Ky. d/1-α-tocopherol was obtained from DSM Nutritional Products, Ltd of Geleen, Netherlands. The GUR 1050 was mechanically blended with the d/1-α-tocopherol using a High Intensity Mixer, available from Eirich Machines of Gurnee, Ill. The GUR 1050 resin was mixed with the d/1-α-tocopherol to create UHMWPE blends having 0.2, 0.5, or 1.0 weight percent d/1-α-tocopherol. The UHMWPE blends were then compression molded to form pucks that were then machined to form cubes having 5 mm sides. The UHMWPE cubes were then heated to a preheat temperature selected from 40° C., 100° C., and 110° C. Once heated to the selected preheat temperature, the UHMWPE blends were irradiated using Method C, set forth in TABLE 2 above, until a total irradiation dose was received. The total irradiation dose was selected from of 90 kGy, 120 kGy, 150 kGy, and 200 kGy.

The resulting UHMWPE blend cubes were then studied to investigate the polymer network parameters of the UHMWPE blend by measuring the materials' swell ratio ($q_s$) with a Swell Ratio Tester (SRT), Cambridge Polymer Group (Boston, Mass.), in accordance with ASTM F-2214-02. Knowing $q_s$, the Flory interaction parameter ($\chi_1$), the molar volume of the solvent ($\phi_1$), and the specific volume of the solvent ($\bar{v}$), the crosslink density ($v_x$) and the molecular weight between crosslinks ($M_c$) of the material were calculated according the following equations:

$$v_x = -\frac{\ln 1 - q_s^{-1} + q_s^{-1} + X_1 q_s^{-2}}{\varphi_1 q_s^{-1/3} - q_s^{-1}/2}$$

$$M_c = \bar{v} v_x$$

Additionally, the swell ratio in stabilized o-xylene at 130° C. was measured in the compression molded direction. The results of the testing are set forth in TABLE 13 below. For example, it was found that a UHMWPE blend having nominally 1.0% weight percent of d/1-α-tocopherol when preheated to nominally 40° C. and subsequently electron beam crosslinked with a total dose of nominally 200 kGy has a $q_s$ less than about 4.3, a $v_x$ more than about 0.090 and a $M_c$ less than about 11,142. It was also found that a UHMWPE blend having nominally 1.0% weight percent of d/1-α-tocopherol when preheated to nominally 110° C. and subsequently electron beam crosslinked with a total dose of nominally 200 kGy has a $q_s$ less than about 3.6, a $v_x$ more than about 0.117 and a $M_c$ less than about 8,577.

Also, it was found that a UHMWPE blend having nominally 0.5% weight percent of d/1-α-tocopherol when preheated to nominally 40° C. and subsequently electron beam crosslinked with a total dose of nominally 200 kGy has a $q_s$ less than about 3.8, a $v_x$ more than about 0.119 and a $M_c$ less than about 8,421. It was also found that a UHMWPE blend having nominally 0.5% weight percent of d/1-α-tocopherol when preheated to nominally 110° C. and subsequently electron beam crosslinked with a total dose of nominally 200 kGy has a $q_s$ less than about 3.6, a $v_x$ more than about 0.109 and a $M_c$ less than about 9,166.

Further, it was found that a UHMWPE blend having nominally 0.2% weight percent of d/1-α-tocopherol when preheated to nominally 40° C. and subsequently electron beam crosslinked with a total dose of nominally 200 kGy has a $q_s$ less than about 2.8, a $v_x$ more than about 0.187 and a $M_c$ less than about 5,351. It was also found that the UHMWPE blend having nominally 0.2% weight percent of d/1-α-tocopherol when preheated to nominally 110° C. and subsequently electron beam crosslinked with a total dose of nominally 200 kGy has a $q_s$ less than about 3.0, a $v_x$ more than about 0.164 and a $M_c$ less than about 6,097.

Additionally, it was found that under some conditions the crosslinked UHMWPE blend exhibited a crosslink density of less than 0.200 moles/dm³. Under other conditions, the crosslinked UHMWPE blend having at least 0.1 weight percent antioxidant exhibited a crosslink density of less than 0.190 moles/dm³. Further, under certain conditions, the crosslinked UHMWPE blend having at least 0.1 weight percent antioxidant exhibited a crosslink density of more than 0.200 moles/dm³ and had a molecular weight between crosslinks of less than 11,200 daltons.

TABLE 13

Swell Ratio, Crosslink Density, and Molecular Weight Between Crosslinks

| RUN | MATERIAL TYPE | SAMPLE DOSE (kGy) | PRE-HEAT TEMP (° C.) | PERCENT VITAMIN E | DOSE RATE (kGy-m/min) |
|---|---|---|---|---|---|
| 1 | GUR 1020 | 90 | 40 | 0.2 | 75.00 |
| 2 | GUR 1050 | 90 | 100 | 0.2 | 75.00 |
| 3 | GUR 1050 | 150 | 40 | 0.2 | 75.00 |
| 4 | GUR 1020 | 150 | 100 | 0.2 | 75.00 |
| 5 | GUR 1020 | 90 | 40 | 1.0 | 75.00 |
| 6 | GUR 1020 | 90 | 100 | 0.5 | 75.00 |
| 7 | GUR 1020 | 150 | 40 | 0.5 | 75.00 |
| 8 | GUR 1020 | 150 | 100 | 1.0 | 75.00 |
| 9 | GUR 1050 | 90 | 40 | 0.2 | 240.00 |
| 10 | GUR 1020 | 90 | 100 | 0.2 | 240.00 |
| 11 | GUR 1020 | 150 | 40 | 0.2 | 240.00 |
| 12 | GUR 1050 | 150 | 100 | 0.2 | 240.00 |
| 13 | GUR 1050 | 90 | 40 | 1.0 | 240.00 |
| 14 | GUR 1020 | 90 | 100 | 1.0 | 240.00 |
| 15 | GUR 1020 | 150 | 40 | 1.0 | 240.00 |
| 16 | GUR 1020 | 150 | 100 | 0.5 | 240.00 |
| 17 | GUR 1050 | 120 | 40 | 0.5 | 157.50 |
| 18 | GUR 1050 | 120 | 100 | 1.0 | 157.50 |
| 19 | GUR 1050 | 120 | 40 | 1.0 | 157.50 |
| 20 | GUR 1050 | 120 | 100 | 1.0 | 157.50 |
| 21 | GUR 1050 | 90 | 40 | 1.0 | 75.00 |
| 22 | GUR 1050 | 90 | 100 | 0.5 | 75.00 |
| 23 | GUR 1050 | 150 | 40 | 0.5 | 75.00 |
| 24 | GUR 1050 | 150 | 100 | 1.0 | 75.00 |
| 25 | GUR 1050 | 90 | 40 | 0.5 | 240.00 |
| 26 | GUR 1050 | 90 | 100 | 1.0 | 240.00 |
| 27 | GUR 1050 | 150 | 40 | 1.0 | 240.00 |
| 28 | GUR 1050 | 150 | 100 | 0.5 | 240.00 |
| 29 | GUR 1050 | 2 × 100 = 200 | 40 | 0.2 | 240.00 |
| 30 | GUR 1050 | 2 × 100 = 200 | 110 | 0.2 | 240.00 |
| 31 | GUR 1050 | 2 × 100 = 200 | 40 | 1.0 | 240.00 |
| 32 | GUR 1050 | 2 × 100 = 200 | 110 | 1.0 | 240.00 |
| 33 | GUR 1050 | 2 × 100 = 200 | 40 | 0.5 | 240.00 |
| 34 | GUR 1050 | 2 × 100 = 200 | 110 | 0.5 | 240.00 |

| RUN | POD WEAR mg/1M CYCLES | SWELL RATIO V/Vo = q(s) | X | Vx = XLD moles/dm^3 | Mc = MWbXL Daltons |
|---|---|---|---|---|---|
| 1 | | 5.09 | 0.44 | 0.068 | 14747 |
| 2 | | 3.40 | 0.49 | 0.129 | 7764 |
| 3 | 2.65 | 3.15 | 0.50 | 0.147 | 6812 |
| 4 | 1.13 | 4.61 | 0.45 | 0.079 | 12652 |
| 5 | | 6.15 | 0.42 | 0.051 | 19720 |
| 6 | | 5.52 | 0.43 | 0.060 | 16706 |
| 7 | | 4.22 | 0.46 | 0.091 | 11019 |
| 8 | | 5.52 | 0.43 | 0.060 | 16706 |
| 9 | | 3.75 | 0.48 | 0.110 | 9126 |
| 10 | | 4.49 | 0.45 | 0.082 | 12143 |
| 11 | | 3.84 | 0.47 | 0.105 | 9483 |
| 12 | 0.17 | 3.23 | 0.50 | 0.141 | 7115 |
| 13 | | 7.13 | 0.41 | 0.040 | 24747 |
| 14 | | 4.47 | 0.45 | 0.083 | 12059 |
| 15 | | 5.69 | 0.43 | 0.057 | 17502 |
| 16 | | 4.46 | 0.45 | 0.083 | 12017 |
| 17 | | 4.50 | 0.45 | 0.082 | 12185 |
| 18 | | 3.74 | 0.48 | 0.110 | 9087 |
| 19 | | 5.32 | 0.43 | 0.063 | 15785 |
| 20 | | 3.33 | 0.50 | 0.133 | 7496 |
| 21 | | 5.78 | 0.43 | 0.056 | 17929 |
| 22 | | 4.43 | 0.45 | 0.084 | 11891 |
| 23 | 3.92 | 3.84 | 0.47 | 0.105 | 9483 |
| 24 | | 3.88 | 0.47 | 0.104 | 9642 |
| 25 | | 5.59 | 0.43 | 0.059 | 17033 |
| 26 | | 4.52 | 0.45 | 0.082 | 12270 |
| 27 | | 4.37 | 0.46 | 0.086 | 11640 |
| 28 | 1.63 | 3.65 | 0.48 | 0.115 | 8733 |
| 29 | 0.02 | 2.76 | 0.53 | 0.187 | 5351 |
| 30 | 0.09 | 2.96 | 0.52 | 0.164 | 6097 |
| 31 | 1.46 | 4.25 | 0.46 | 0.090 | 11142 |
| 32 | 0.64 | 3.61 | 0.48 | 0.117 | 8577 |
| 33 | | 3.57 | 0.48 | 0.119 | 8421 |
| 34 | | 3.76 | 0.48 | 0.109 | 9166 |

What is claimed is:

1. An antioxidant-stabilized crosslinked ultra-high molecular weight polyethylene, comprising:
   crosslinked polyethylene comprising tocopherol or a salt or ester thereof that has reacted with a free-radical on the polyethylene; and unreacted tocopherol, or a salt or ester thereof;
wherein the antioxidant-stabilized crosslinked polyethylene has a pin-on-disc wear rate of about 0.02 mg/Mc to about 0.69 mg/Mc.

2. The antioxidant-stabilized crosslinked polyethylene of claim 1, wherein the tocopherol ester is tocopherol acetate.

3. The antioxidant-stabilized crosslinked polyethylene of claim 1, wherein the unreacted tocopherol ester is tocopherol acetate.

4. The antioxidant-stabilized crosslinked polyethylene of claim 3, wherein $R^1$ and $R^2$ are methyl.

5. The antioxidant-stabilized crosslinked polyethylene of claim 1, wherein the tocopherol that has reacted with the free radical is d,l-α-tocopherol or an acetate ester thereof.

6. The antioxidant-stabilized crosslinked polyethylene of claim 1, wherein the unreacted tocopherol is d,l-α-tocopherol.

7. The antioxidant-stabilized crosslinked polyethylene of claim 1, wherein the unreacted tocopherol or salt or ester thereof is contained within the crosslinked polyethylene.

8. The antioxidant-stabilized crosslinked polyethylene of claim 1, wherein the tocopherol or salt or ester thereof that has reacted with the free radical is homogenously distributed within the crosslinked polyethylene.

9. The antioxidant-stabilized crosslinked polyethylene of claim 1, wherein the unreacted tocopherol or salt or ester thereof has antioxidant activity.

10. The antioxidant-stabilized crosslinked polyethylene of claim 1, wherein about 0.028 wt % to about 0.882 wt % of the crosslinked polyethylene is a combination of the tocopherol or salt or ester thereof that has reacted with the free radical and the unreacted tocopherol or salt or ester thereof.

11. The antioxidant-stabilized crosslinked polyethylene of claim 1, wherein the crosslinking comprises irradiation.

12. The antioxidant-stabilized crosslinked polyethylene of claim 1, wherein the crosslinking comprises electron beam irradiation or gamma irradiation.

13. The antioxidant-stabilized crosslinked polyethylene of claim 1, wherein the antioxidant-stabilized crosslinked polyethylene has a pin-on-disc wear rate of 0.09 mg/Mc to about 0.62 mg/Mc.

14. The antioxidant-stabilized crosslinked polyethylene of claim 1, wherein the antioxidant-stabilized crosslinked polyethylene has a pin-on-disc wear rate of about 0.02 mg/Mc to about 0.64 mg/Mc.

15. The antioxidant-stabilized crosslinked polyethylene of claim 1, wherein the antioxidant-stabilized crosslinked polyethylene is molded into at least one of a substrate, a polymeric article, and an antioxidant-stabilized polymeric article.

16. An orthopedic implant comprising the antioxidant-stabilized crosslinked polyethylene of claim 1.

* * * * *

UNITED STATES PATENT AND TRADEMARK OFFICE
CERTIFICATE OF CORRECTION

PATENT NO. : 9,265,545 B2
APPLICATION NO. : 14/157708
DATED : February 23, 2016
INVENTOR(S) : Rufner et al.

It is certified that error appears in the above-identified patent and that said Letters Patent is hereby corrected as shown below:

Title Page, item (56),

On page 4, in column 2, under "Other Publications", line 29, delete "Applicatlon" and insert --Application--, therefor On page 4, in column 2, under "Other Publications", line 29, delete "malled" and insert --mailed--, therefor On page 4, in column 2, under "Other Publications", line 33, delete "malled" and insert --mailed--, therefor On page 4, in column 2, under "Other Publications", line 46, delete "Actlon" and insert --Action--, therefor On page 5, in column 2, under "Other Publications", line 52, delete "Morecular" and insert --Molecular--, therefor On page 5, in column 2, under "Other Publications", line 56, delete "molecularweight" and insert --molecular weight--, therefor On page 5, in column 2, under "Other Publications", line 57, delete "a-tocopherol" and insert --α-tocopherol--, therefor On page 5, in column 2, under "Other Publications", line 60, delete "a-tocopherol" and insert --α-tocopherol--, therefor On page 5, in column 2, under "Other Publications", line 62, delete "Biomatyerials," and insert --Biomaterials,--, therefor Signed and Sealed this
Sixteenth Day of August, 2016

Michelle K. Lee
*Director of the United States Patent and Trademark Office*

On page 6, in column 1, under "Other Publications", line 4, delete "a-Tocopherol" and insert --α-Tocopherol--, therefor On page 6, in column 1, under "Other Publications", line 19, delete "a-tocopherol" and insert --α-tocopherol--, therefor On page 6, in column 1, under "Other Publications", line 50, delete "May" and insert --Jan.--, therefor In the Claims In column 32, line 13, in Claim 13, after "rate of", insert --about--, therefor